US00PP36033P2

(12) United States Plant Patent
Milla-Lewis

(10) Patent No.: US PP36,033 P2
(45) Date of Patent: Jul. 23, 2024

(54) ST. AUGUSTINEGRASS PLANT NAMED 'XSA 11377'

(50) Latin Name: ***Stenotaphrum secundatum* (Walt.) Kuntze**
Varietal Denomination: XSA 11377

(71) Applicant: North Carolina State University, Raleigh, NC (US)

(72) Inventor: Susana Milla-Lewis, Apex, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/445,230

(22) Filed: Jun. 6, 2023

(51) Int. Cl.
*A01H 5/12* (2018.01)
*A01H 6/00* (2018.01)

(52) U.S. Cl.
USPC ..... Plt./392

(58) Field of Classification Search
USPC ..... Plt./392
See application file for complete search history.

(56) References Cited

PUBLICATIONS

Van der Laat, R. et al. "Variation in southern chinch bug (Blissus insularis) survival and damage on St. Augustinegrass germplasm", Apr. 29, 2021, International Turfgrass Society Research Journal; vol. 14, issue 1, p. 642-651 URL: https://onlinelibrary.wiley.com/doi/epdf/10.1002/its2.67.*
"NC State University Releases Sola™, the Newest St.Augustinegrass" https://cals.ncsu.edu/crop-and-soil-sciences/news/nc-state-university-releases-sola-the-newest-st-augustinegrass/ (7 pages) (Aug. 15, 2022).
Sod Solutions Professionals "NC State University Releases Sola™, the Newest St.Augustinegrass" https://sodsolutionspro.com/nc-state-university-releases-sola-the-newest-st-augustinegrass/ (8 pages) (2022).
Busey, et al., "Genetic and environmental determinants of zoysiagrass adaptation in a subtropical region", The Journal of the American Society for Horticultural Science, 107:79-82, 1982.
Busey, Philip , "St. Augustinegrass, *Stenotaphrum secundatum* (Walt.) Kuntze", pp. 309-329 In: MD Casler and RR Duncan, Turfgrass Biology, Genetics, and Breeding, John Wiley & Sons, Hoboken, NJ (2003).
Busey , et al., "Turfgrass in the shade environment", Proceedings of the Florida State Horticultural Society, 104:353-358, 1991.
Carbajal , et al., "Identification of sources of resistance to gray leaf spot in *Stenotaphrum* germplasm", Crop Science, 61:3069-3079, 2021.
Dice, Lee R., "Measures of the Amount of Ecologic Association Between Species", Ecology, 26:297-302, 1945.
Jha, Puja , "Assessing sod production characteristics: sod handling quality and sod tensile strength of warm-season turfgrasses", MS Thesis from Oklahoma State University (72 pages) (Dec. 2018).
Milla-Lewis , et al., "Cytological and molecular characterization of genetic diversity in *Stenotaphrum*", Crop Science, 53(1):296-308, 2013.
Miller, Grady , "2023 Sod producers' report for North Carolina", NC State Extension Publication AG-809 (10 pages) (Jun. 8, 2023).
Morris , et al., "NTEP turfgrass evaluation guidelines", https://www.ntep.org/pdf/ratings.pdf (5 pages) (1998).
Mulkey , et al., "Development and characterization of simple sequence repeat (SSR) markers for St. Augustinegrass (*Stenotaphrum secundatum* (Walt.) Kuntze)", Crop Science, 54:401-412, 2014.
Mulkey , et al., "Genetic analysis of a St. Augustinegrass germplasm collection using AFLP markers and flow cytometry", International Turfgrass Society Research Journal, 12:281-291, 2013.
Rohlf, James F., "NTSYS-PC: Numerical Taxonomy and Multivariate Analysis System: Getting Started Guide", Department of Ecology and Evolution State University of New York, Version 2.2. Exeter Software, Setauket, NY. (2000).
Sokal , et al., "A Statistical Method for Evaluating Systematic Relationships", The University of Kansas Science Bulletin, 28(22):1409-1438, 1958.

* cited by examiner

*Primary Examiner* — Susan McCormick Ewoldt
*Assistant Examiner* — Zachariah Allan Kay
(74) *Attorney, Agent, or Firm* — Myers Bigel, P.A.

(57) ABSTRACT

'XSA 11377' is a new St. Augustinegrass cultivar that is fast to establish, has good levels of shade and drought tolerances, and has superior turf quality. It is distinguishable from other cultivars by its medium-fine texture, aggressive stoloniferous growth, improved sod strength, and improved shade tolerance. 'XSA 11377' shows gray leaf spot and chinch bug tolerance, and maintains above average turf quality under normal management practices. 'XSA-11377' is also genetically distinct from other St. Augustinegrass cultivars currently in the marketplace known to the Inventor.

29 Drawing Sheets

Specification includes a Sequence Listing.

STATEMENT OF GOVERNMENT SUPPORT

This invention was made with government support under grant number 2019-51181-30472 awarded by the National Institute of Food and Agriculture (USDA/NIFA). The government has certain rights in the invention.

Latin name of the genus and species: The Latin name of the novel grass cultivar disclosed herein is *Stenotaphrum secundatum* (Walt.) Kuntze.

Variety denomination: The inventive cultivar of *Stenotaphrum secundatum* disclosed herein has been given the varietal denomination 'XSA 11377'.

STATEMENT REGARDING ELECTRONIC FILING OF A SEQUENCE LISTING

A Sequence Listing in XML format, entitled 5051-1016_ST26.xml, 29,061 bytes in size, generated on Oct. 5, 2023, and filed herewith, is hereby incorporated by reference in its entirety for its disclosures.

BACKGROUND OF THE INVENTION

'XSA 11377' is a new St. Augustinegrass cultivar that is fast to establish, has good levels of shade and drought tolerances, and has superior turf quality. Furthermore, this cultivar has gray leaf spot and chinch bug tolerance, improved sod strength, and maintains above average turf quality under normal management practices. It comprises traits well suited for home lawns and landscapes in the southern US and into the transition zone.

SUMMARY OF THE INVENTION

'XSA 11377' is a perennial St. Augustinegrass that spreads by stolons and was identified in 2013 because of its superior turf quality and aggressive growth from a collection of St. Augustinegrass plants that were evaluated under cultivated conditions in Raleigh, Jackson Springs, and Laurel Springs, North Carolina. 'XSA 11377' can be distinguished from other St. Augustinegrasses by its medium-fine texture, aggressive stoloniferous growth, superior sod strength, and improved shade tolerance. Additionally, Simple Sequence Repeat (SSR) data shows 'XSA 11377' is genetically distinct from all major St. Augustinegrass cultivars currently on the market known to the Inventor. 'XSA 11377' is fast to establish, has good levels of shade and drought tolerances, and has superior turf quality over St. Augustinegrass cultivar 'Raleigh'. Furthermore, in comparison to 'Raleigh', this cultivar has better gray leaf spot and chinch bug tolerance, and significantly better sod strength, traits that are desirable to reduce management costs and increase harvest ability in sod production.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Stenotaphrum secundatum* St. Augustinegrass 'XSA 11377'.

FIG. 7A shows final establishment on year 1, FIG. 7B shows drought tolerance, FIG. 7C shows gray leaf spot incidence, and FIG. 7D shows Southern Chinch Bug tolerance evaluated in replicated trials at the Raleigh, NC, Jackson Springs, NC, and Laurel Springs, NC sites. Filled circles on graphs correspond to commercial cultivars used for comparison ("checks"), while filled triangles correspond to experimental lines including 'XSA 11377'.

DETAILED BOTANICAL DESCRIPTION OF THE NEW VARIETY

Figure 1:
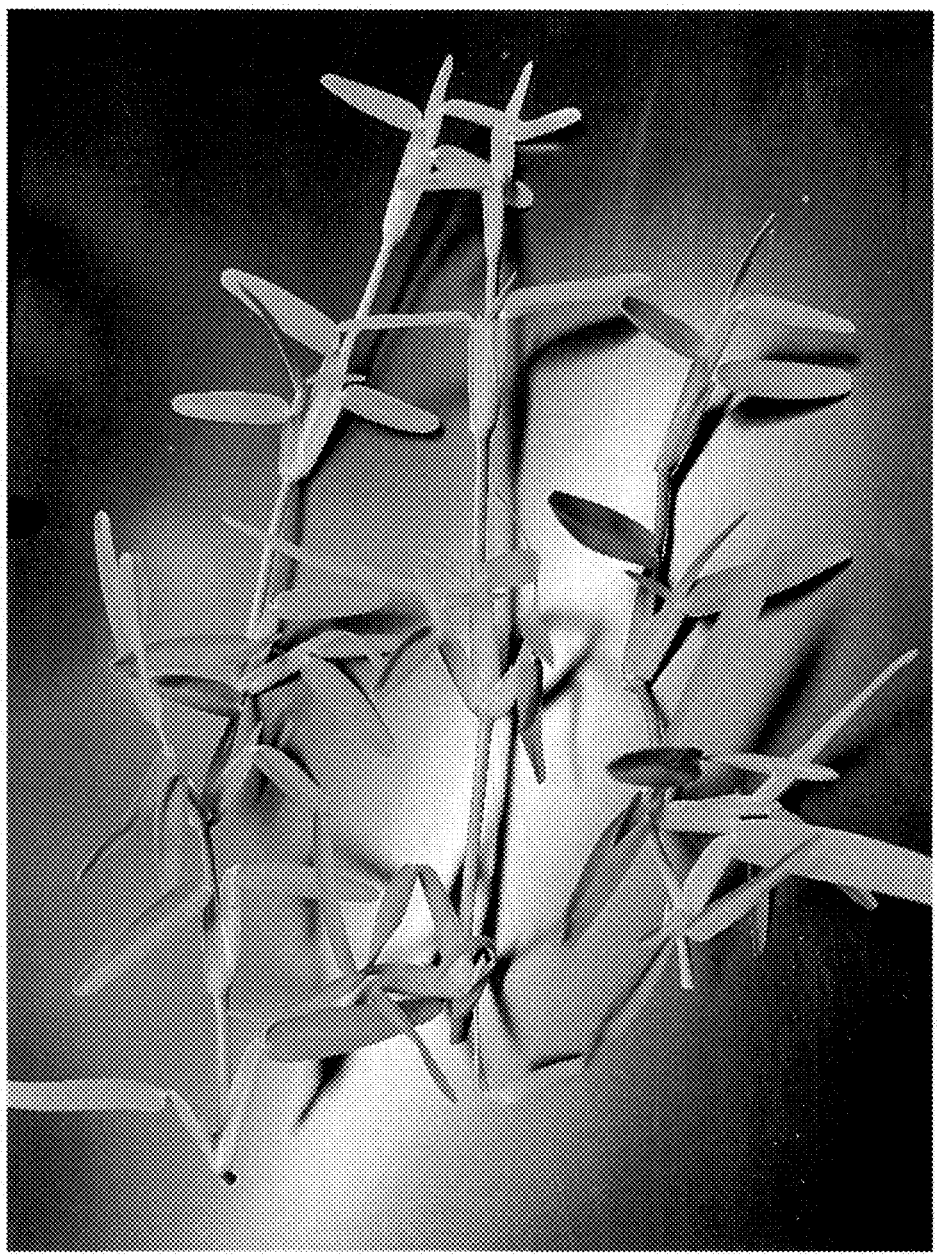
FIG. 1 is a color photograph of stolons of a typical specimen of the claimed plant.

The following is a detailed description of the botanical characteristics of a new and distinct cultivar of *Stenotaphrum secundatum* St. Augustinegrass plant known by the cultivar name 'XSA 11377'. All colors cited herein refer to The Royal Horticulture Society Colour Chart designations (The Royal Horticultural Society, London, Flower Council of Holland 1986 edition) except where general terms of ordinary dictionary significance are used. Where dimensions, sizes, colors, and other characteristics are given, it is to be understood that such characteristics are approximations or averages set forth as accurately as practicable.

This invention relates to a new and unique cultivar of perennial St. Augustinegrass (*Stenotaphrum secundatum* (Walt.) Kuntze) designated as 'XSA 11377'. 'XSA 11377' is an F1 hybrid that was produced in Raleigh, North Carolina (NC) in the Fall of 2011 by crossing cultivar 'Raleigh' (unpatented) as the female parent with pollen of plant introduction (PI) 410353 (National Plant Germplasm System, USDA). Crosses of 'Raleigh' by PI 410353 were manually made in 2011 under greenhouse and laboratory conditions.

'Raleigh' and PI 410353 were grown in greenhouses for production of inflorescences. Once 'Raleigh' started producing tillers with opening inflorescences, the tillers were collected (with at least two internodes and healthy enough for root production) and transported to the laboratory where they were placed in test tubes with water. Test tubes were labeled and placed in a container with humidity over 70% and temperature around 22-25° C. To avoid pollen contamination, anthers were removed twice a day, early in the morning and before making the crosses. In the greenhouses, pollen from PI 410353 was collected in petri dishes and pollen grains were transported to the lab where it was spread on stigmas using a brush. Pollinated flowers reached maturity after four weeks at which time seeds were manually harvested with forceps. Harvested seeds were germinated in petri dishes for six weeks. Seedlings were then transferred to potting soil and grown in the greenhouse, where they reached maturity in azalea pots (6 in. diameter×4¼ in. tall).

'XSA 11377' was first vegetatively propagated in Raleigh, NC in 2012 by rooting nodes and stolons in potting soil. Asexually reproduced plants of 'XSA 11377' have remained stable and true to type through at least 10 successive cycles of vegetative propagation. 'XSA 11377' has been determined to be diploid (2n=2x=18).

'XSA 11377' has not been observed under all possible environmental conditions; therefore, the phenotype may vary under different environmental conditions such as season, temperature, light intensity, day length, cultural conditions, and the like, without however, any variance in the genotype.

Leaf blades:

*Length.*—30 mm.
*Width.*—7 mm.
*Shape.*—Blunt: not hairy.
*Apex.*—Boat shaped.
*Aspect.*—Concave.
*Margin.*—Smooth.
*Auricle.*—Absent.
*Collar.*—Continuous.
*Sheath.*—Open.
*Leaf bud.*—Rolled.
*Ligule type.*—Short fringe of hairs.
*Leaf blade color of adaxial surface.*—RHS 137D: Green-Group.
*Leaf blade color of abaxial surface.*—RHS 137C: Green-Group.
*Venation.*—Parallel.

Stolons:

*Internode length.*—50.8 mm.
*Internode color.*—RHS 199A: Grey-Brown-Group.
*Internode diameter.*—2.5 mm.
*Apical meristem first leaf.*—29.9 mm.
*Node diameter.*—4.4 mm.
*Node color.*—RHS 199B: Grey-Brown-Group.

Inflorescence:

*Inflorescence length.*—4.40 mm.
*Inflorescence color.*—RHS 199A: Grey-Brown-Group.
*Inflorescence diameter.*—5 mm.
*Inflorescence stigmas color.*—RHS 83A: Violet-Group.
*Inflorescence anther color.*—RHS 31A: Orange-Red Group.

Figure 2:
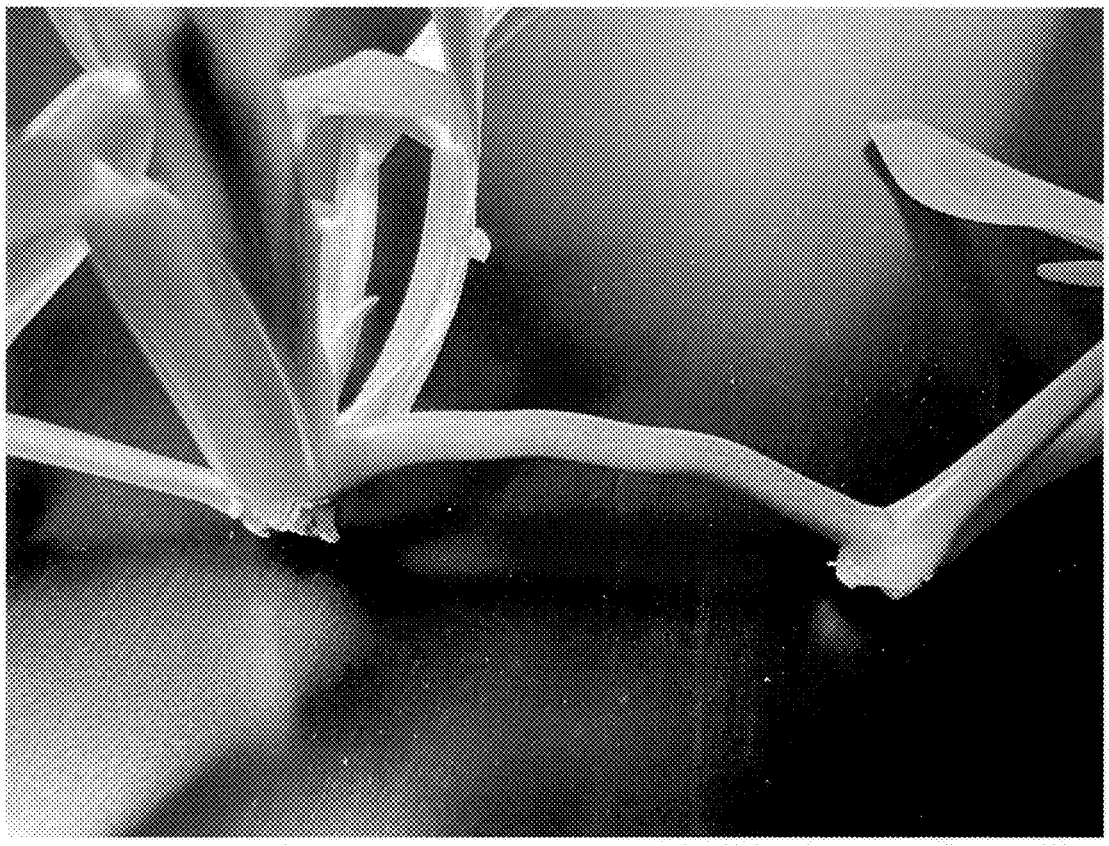
FIG. 2 is a color photograph of a stolon of a typical specimen of the claimed plant.
Figure 3:
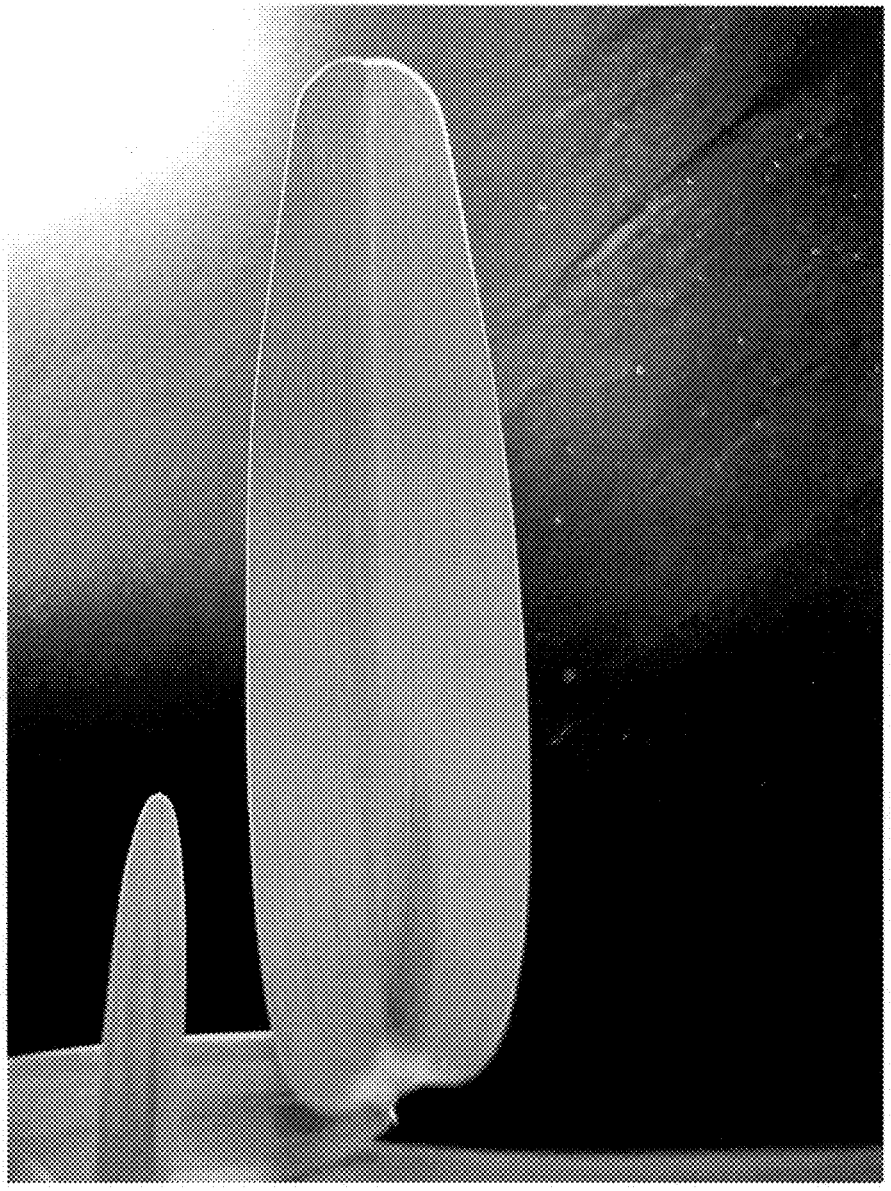
FIG. 3 is a color photograph of leaf blades of a typical specimen of the claimed plant.
Figure 4:
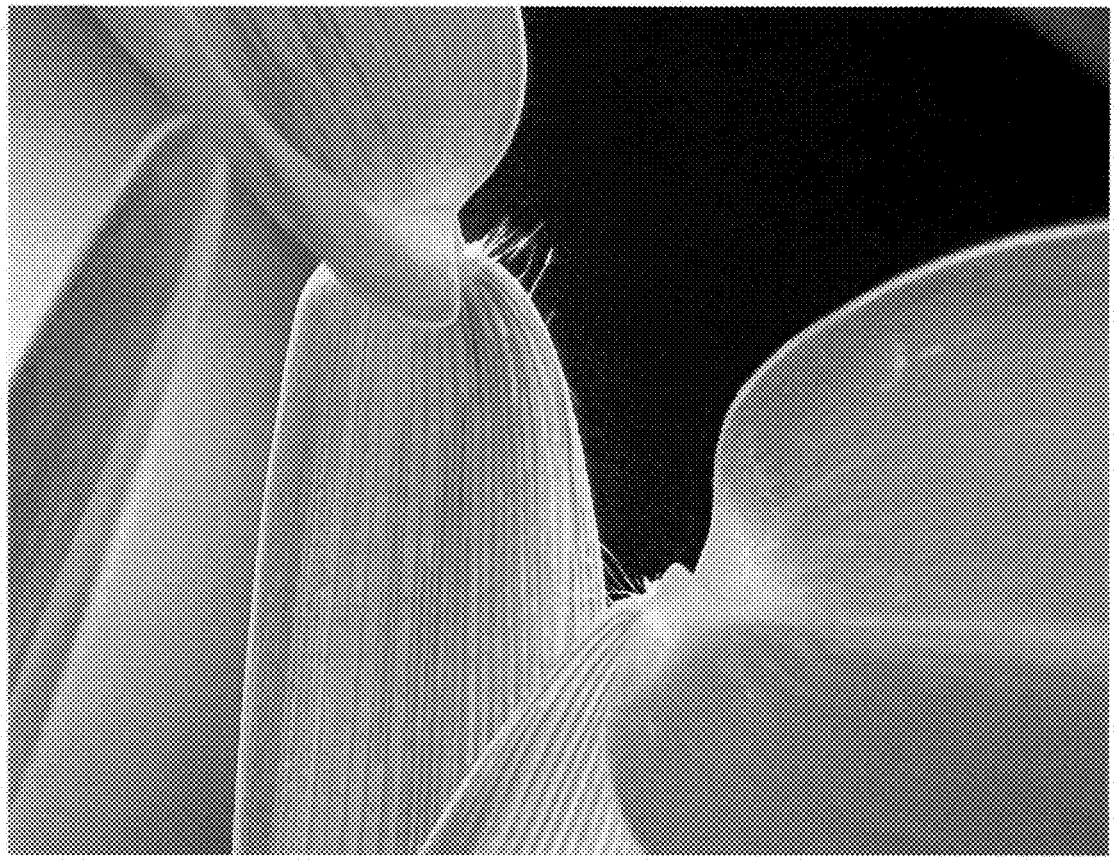
FIG. 4 is a color photograph of hairs of a typical specimen of the claimed plant.
Figure 5A:
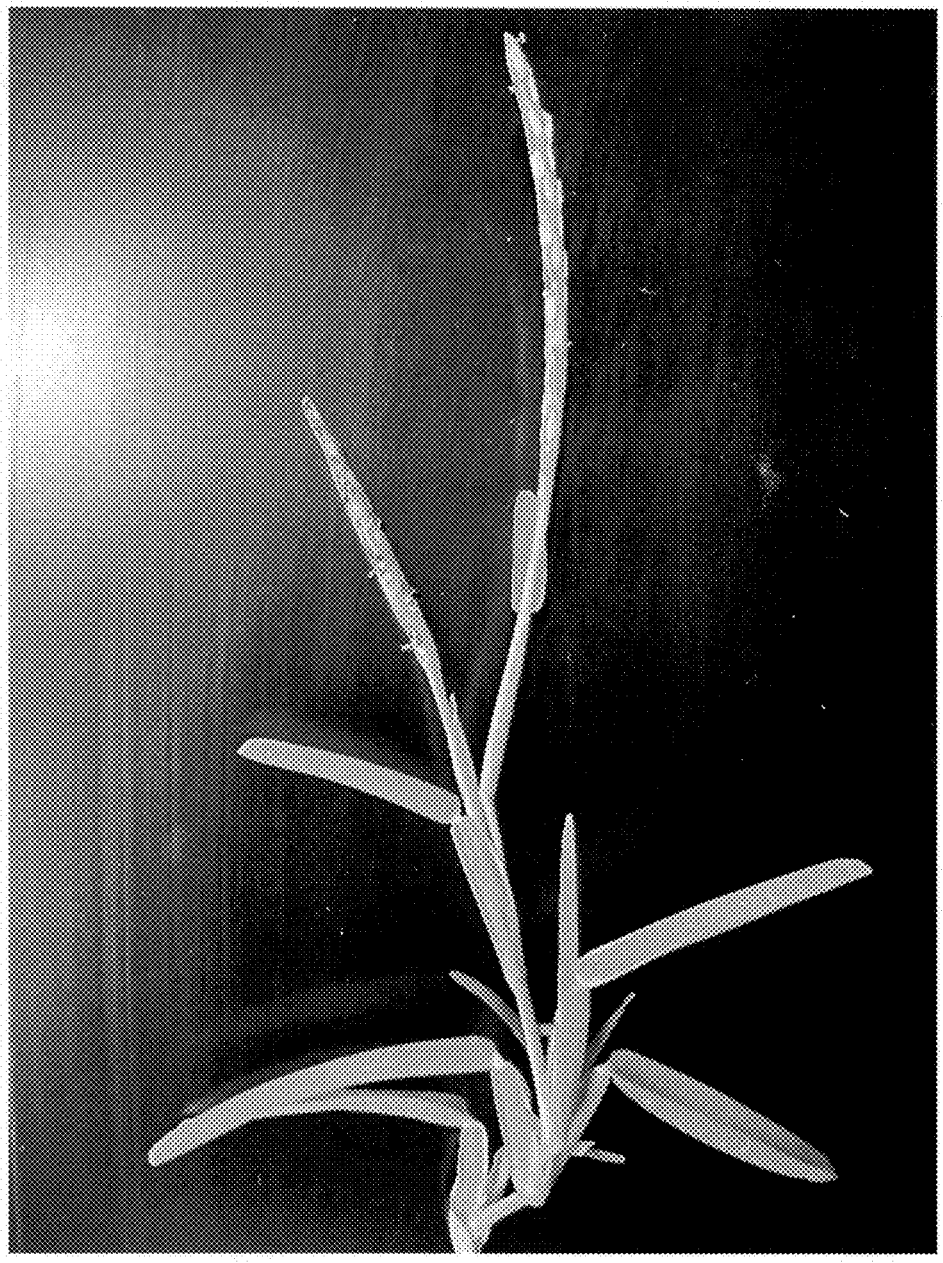
FIGS. 5A-5B are color photographs of inflorescences of a typical specimen of the claimed plant.
Figure 5B:
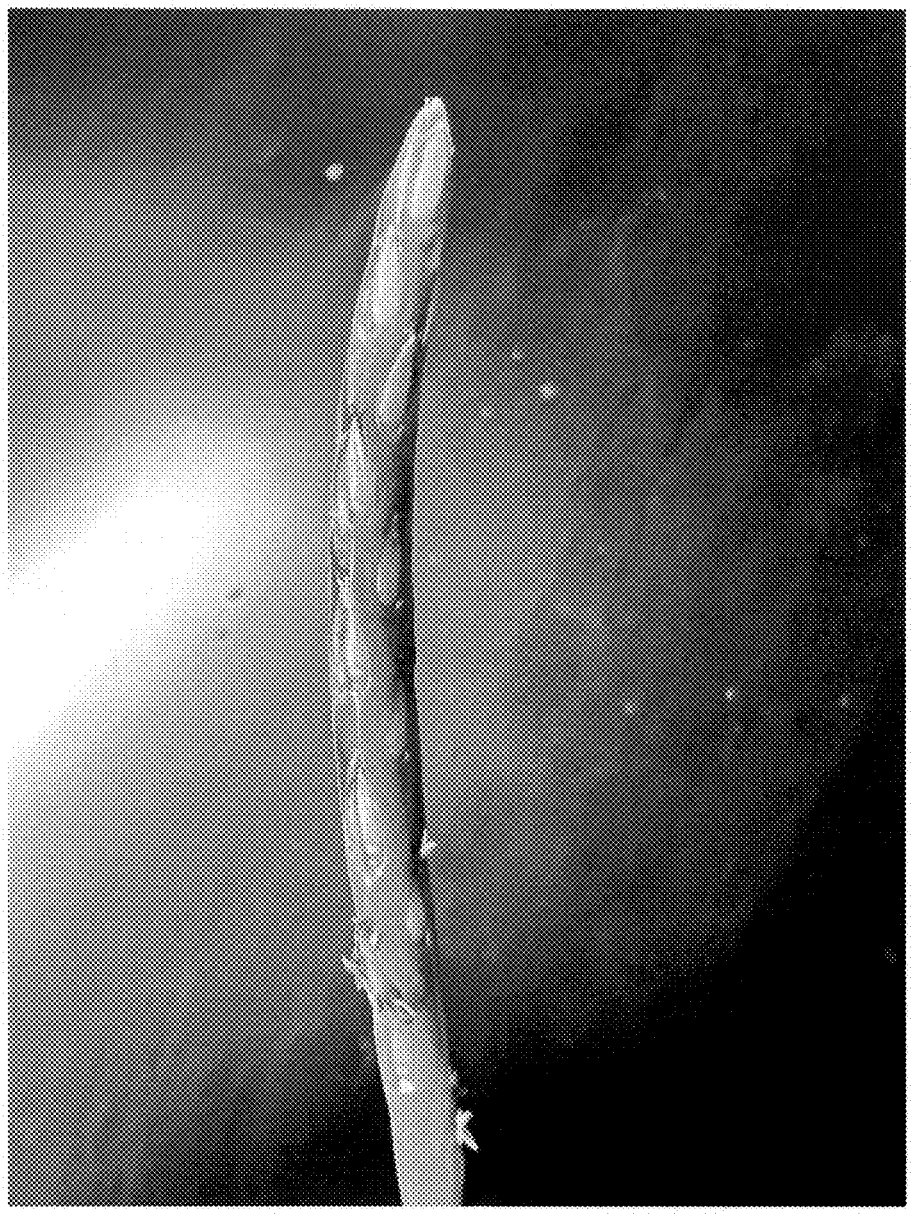
Figure 6A:
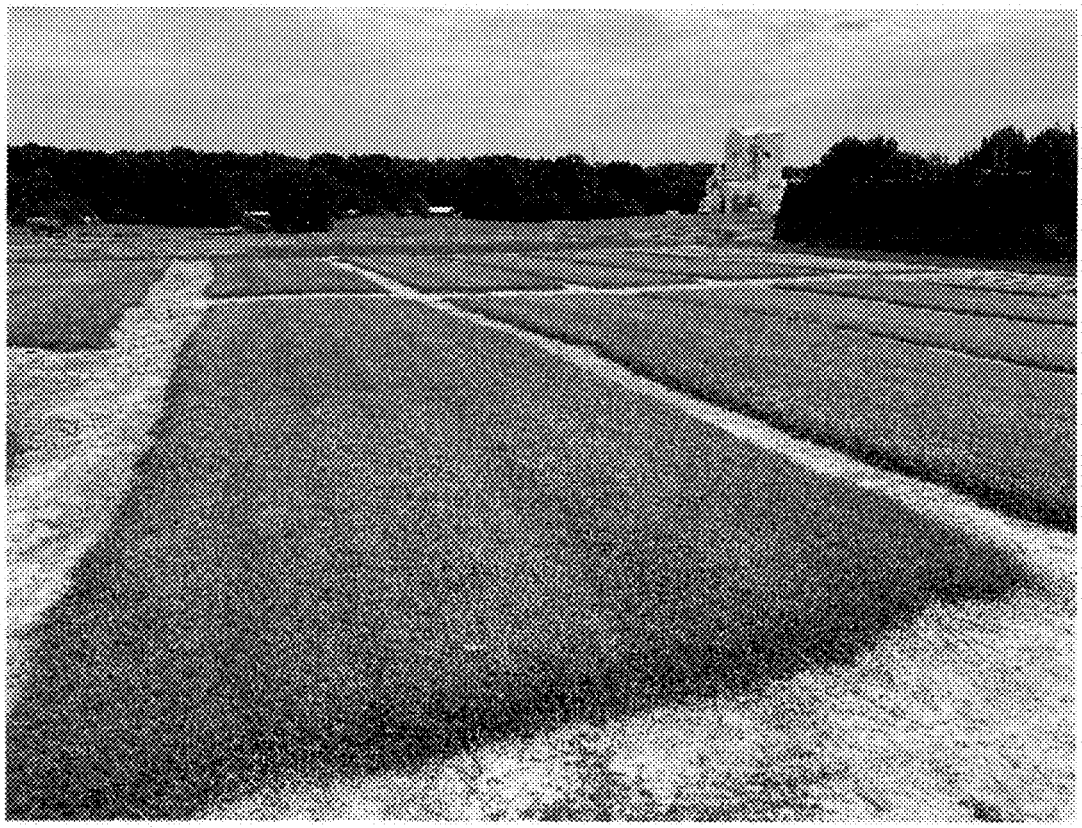
FIGS. 6A-6C are color photographs of plots of a typical specimen of the claimed plant.
Figure 6B:
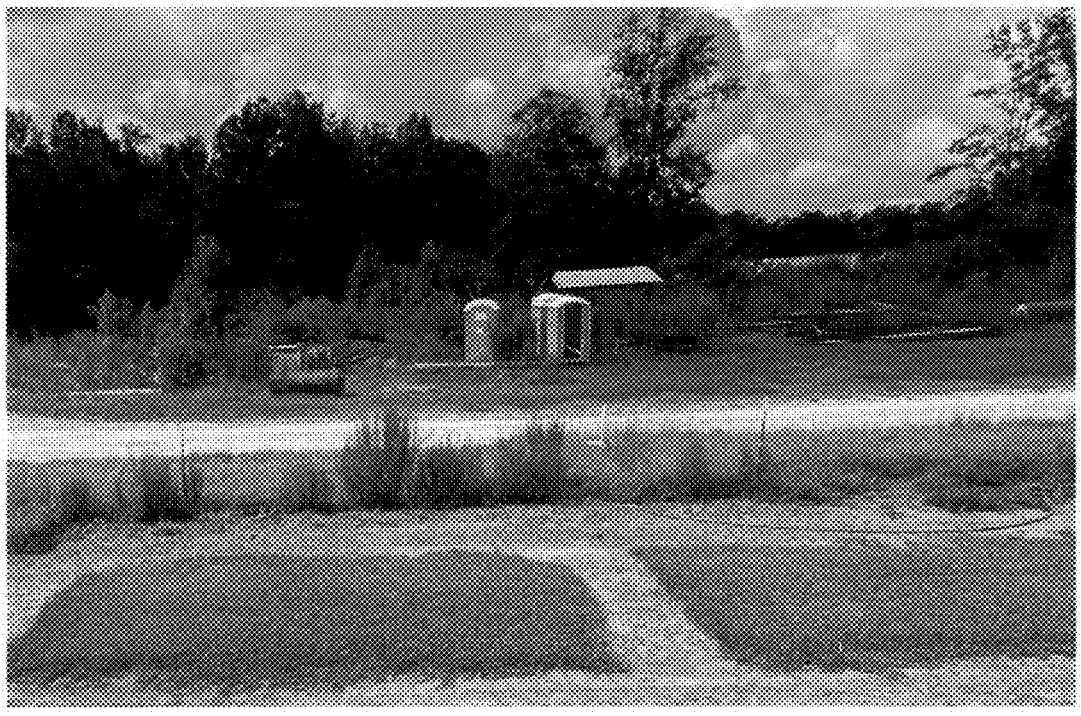
Figure 6C:
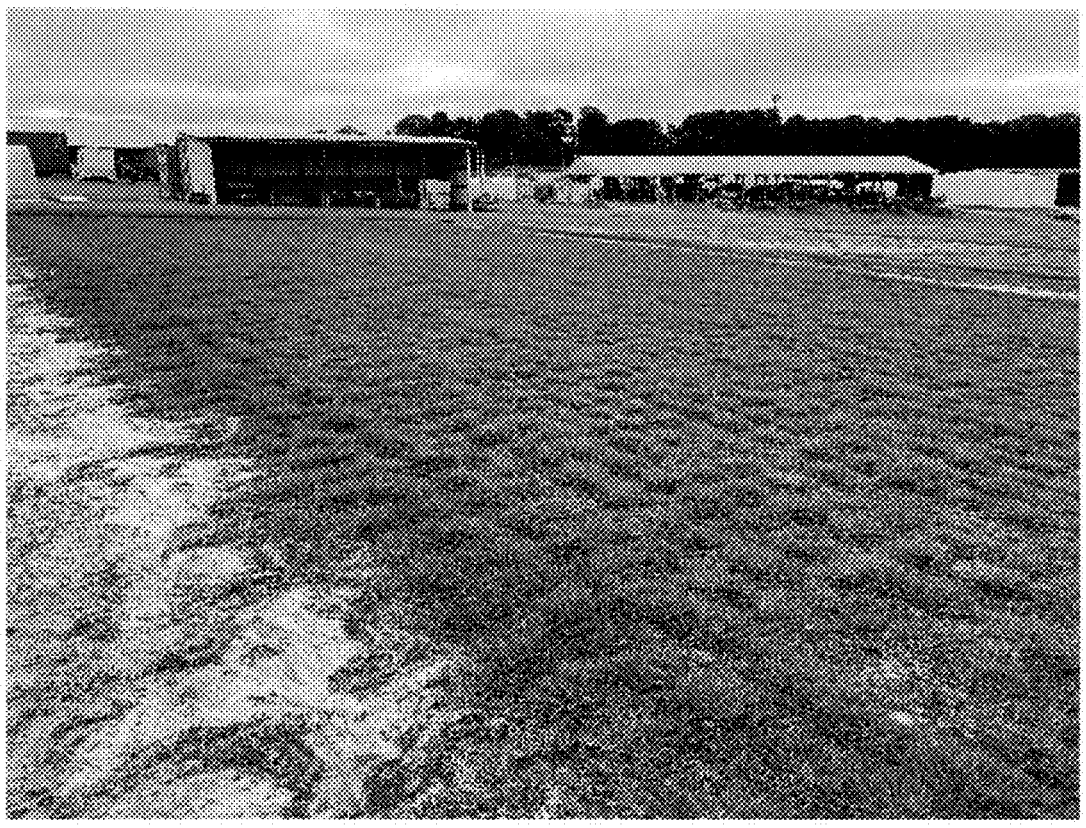
Figure 7A:
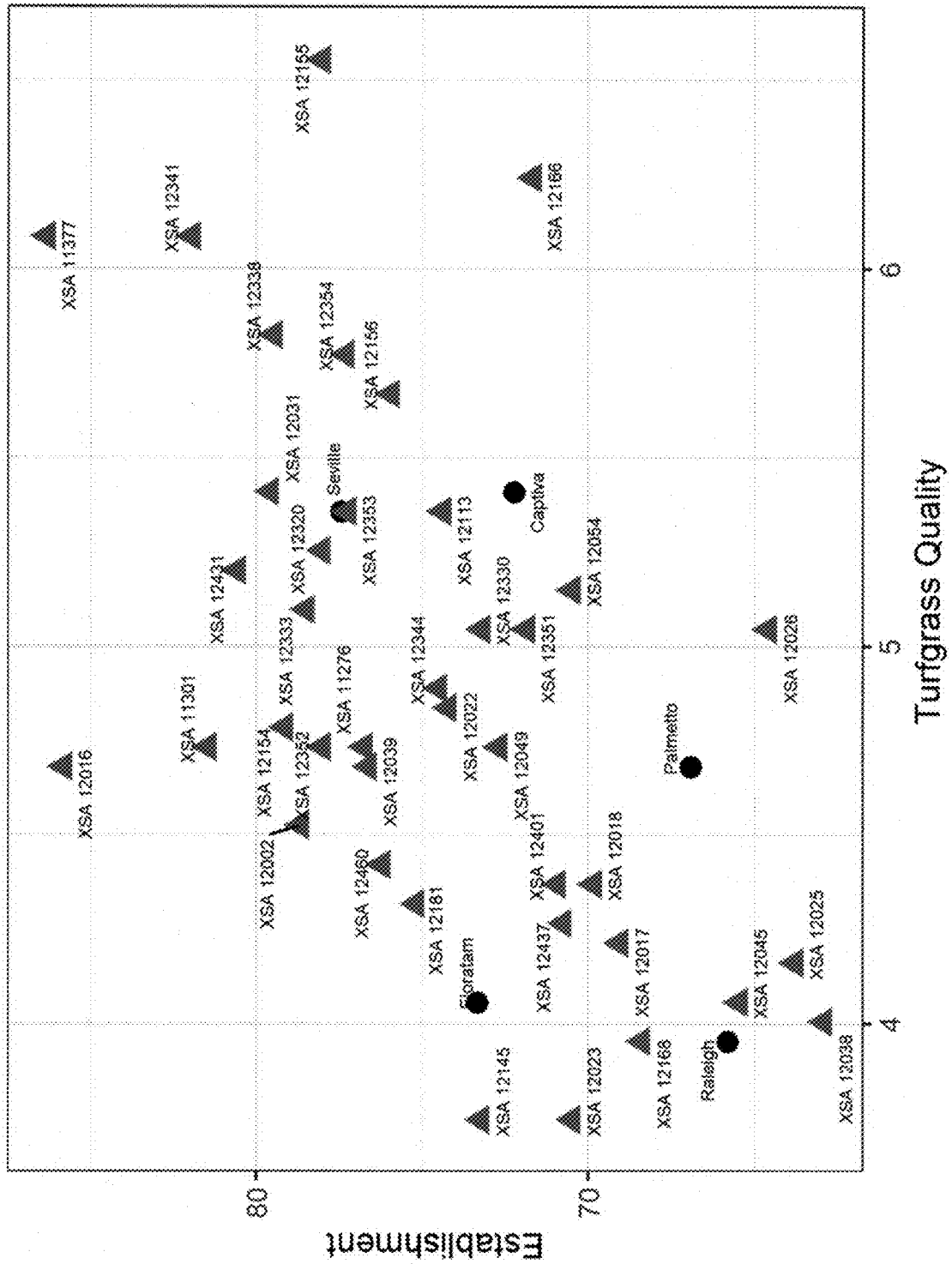
FIGS. 7A-7D show images of data plots representing mean performance across locations of breeding lines and commercial cultivars evaluated for turfgrass quality versus
Figure 7B:
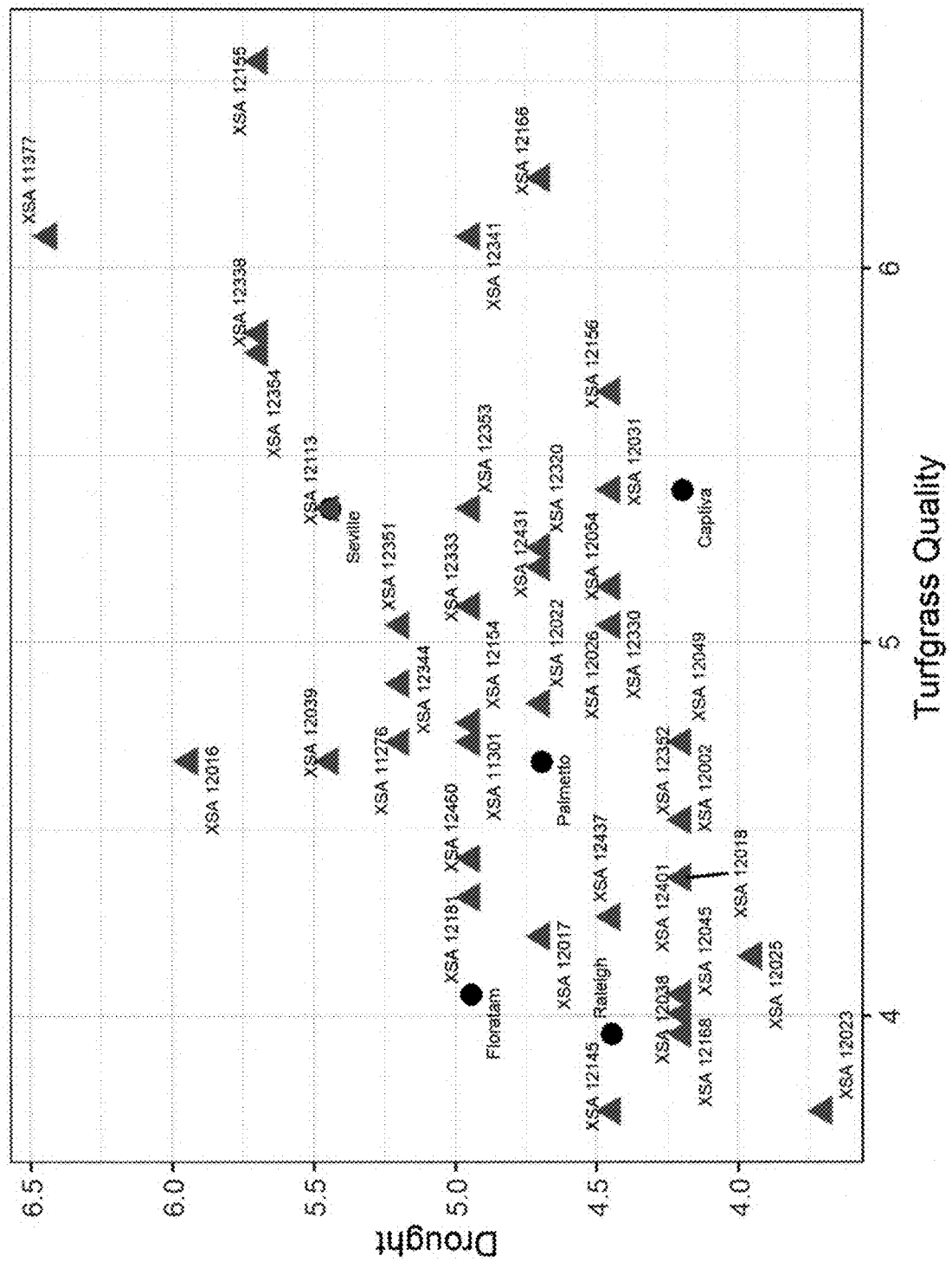
Figure 7C:
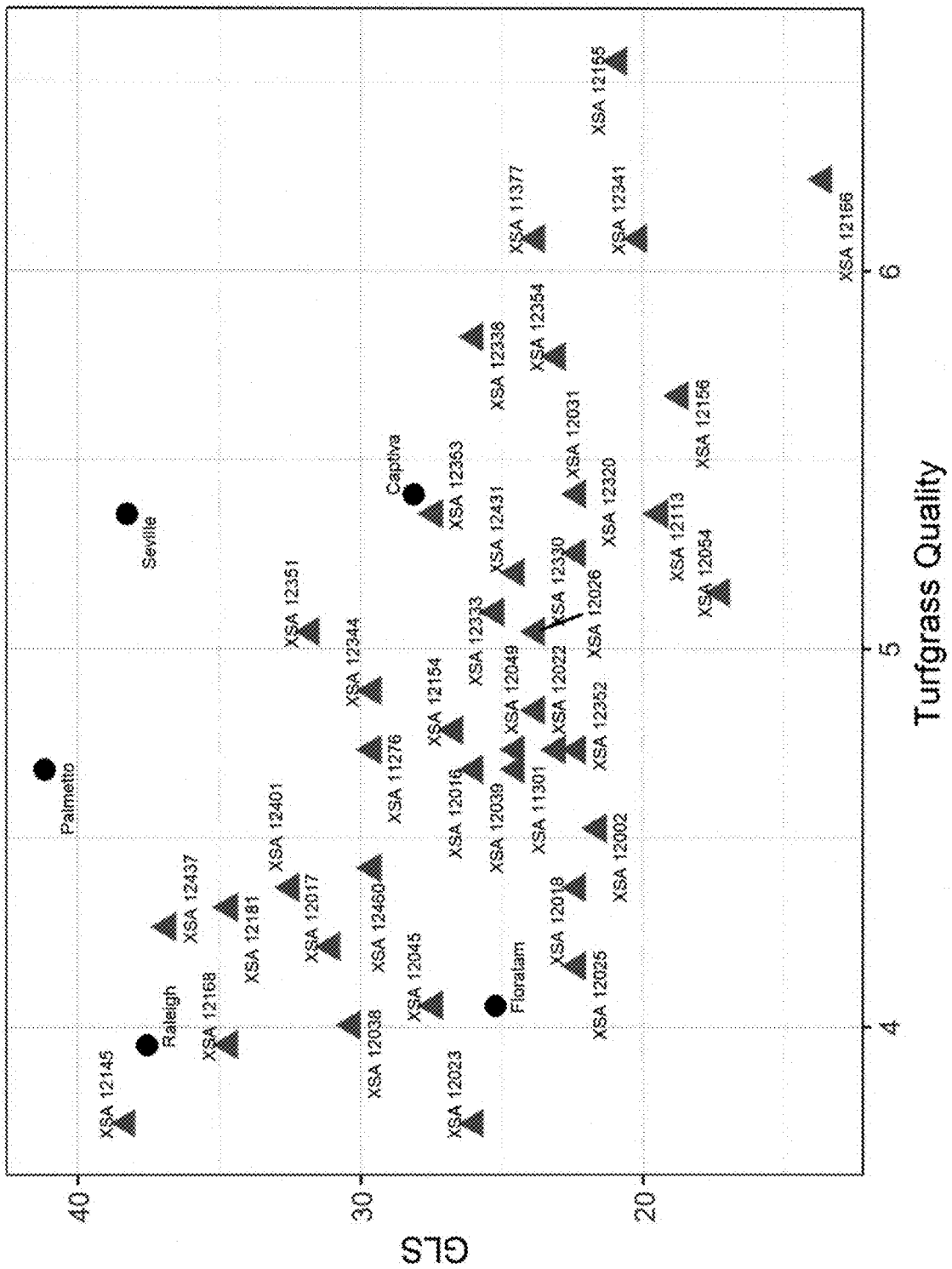
Figure 7D:
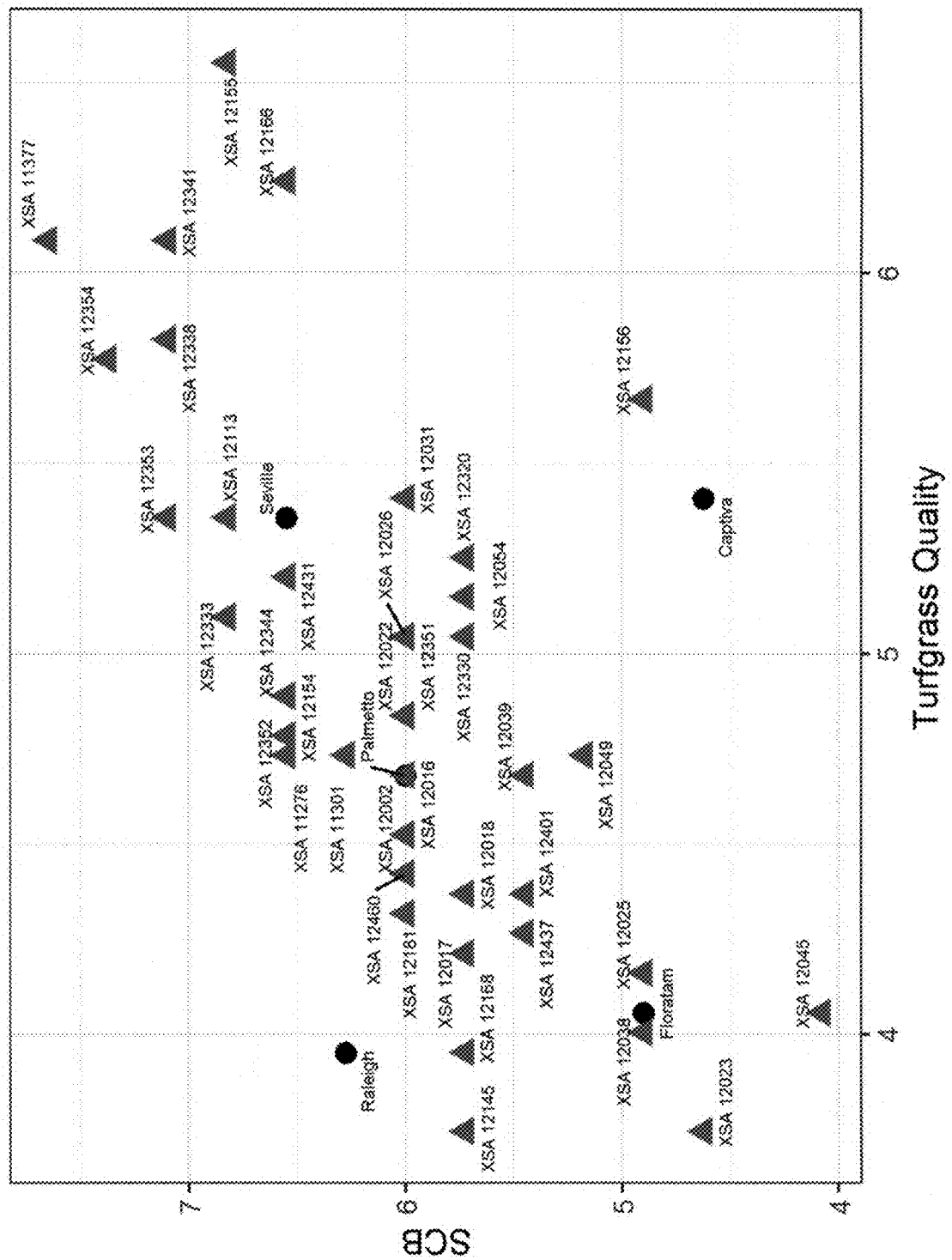

FIGS. 1-6A-6C provide photographic images of the claimed plant. In particular, FIG. 1 shows an example of stolons of a typical specimen of 'XSA 11377'. FIG. 2 shows an example of a singular stolon of a typical specimen of 'XSA 11377'. FIG. 3 shows an example of leaf blades of a typical specimen of 'XSA 11377'. FIG. 4 shows an example of leaf hairs of a typical specimen of 'XSA 11377'. FIGS. 5A-5B show examples of inflorescences of a typical specimen of 'XSA 11377'. FIGS. 6A-6C show examples of plots of a typical specimen of 'XSA 11377'. In particular, FIG. 6A shows conditions under full management at Raleigh, NC, FIG. 6B shows a plot evaluated for sod strength, and FIG. 6C shows a plot of early establishment of a breeders block.

Morphological analysis of 'XSA 11377' and comparison to other St. Augustinegrass cultivars: 'XSA 11377' was morphologically compared to commercial cultivars 'Captiva' [U.S. Plant Pat. No. 21,280 as 'NUF-76'; marketed under tradename Captiva®], 'CitraBlue' [U.S. Plant Pat. No. 32,456 as 'FSA1602'; marketed under tradename CitraBlue®], 'Floratam' [unpatented], 'Palmetto' [U.S. Plant Pat. No. 9,393 as 'SS-100'; marketed under tradename Palmetto™], 'Raleigh' (female parent), 'Seville' [U.S. Plant Pat. No. 4,097], 'TamStar' [U.S. Plant Pat. No. 27,393 as 'DALSA 0605'; marketed under tradename TamStar®], and 'Texas Common' [unpatented]. List of patent statuses of commercial cultivars provided in Table 8. SUNGRO® HOTICULTURE MM830)-F3B 2.8 Cu ft soil enriched with 50-60% sphagnum peat moss, softwood bark, perlite and dolomite limestone was used for propagation. Plant material was propagated into 12.5 cm-diameter by 8.9 cm-deep pots for a total of three pots per entry. Plant materials were established in January 2023 and grown through April 2023 inside a greenhouse in Raleigh NC. 20 to 30° C. Pots were fertilized every 45 days using Turf Builder Southern Lawn Food (32-0-10) from Scotts R. Watering was performed as needed, about four to five times per week. Light requirements included natural sunlight only. Pots were left without mowing to trigger stolon development around the pots. Fifteen weeks after propagation, digital calipers (6 inches precision measuring tool) were used to collect morphological data. Morphological measurements were taken on internode length, internode diameter and node diameter. From each of the three pots per cultivar, nine measurements were collected per trait. Internode diameter and length were measured using the space between the fourth and fifth nodes, while the stolon node diameter was measured at the fourth node. Leaf length and width were collected from the third youngest leaf. In addition, length of the first leaf at the apical meristem was measured separately. Inflorescence measurements were collected on mature spikes with six measurements in total being collected per spike. Collected data were analyzed using LSD ($P \leq 0.05$) in R. Means followed by the same letter are not significantly different at $P=0.05$.

TABLE 1

Internode length (mm) of St. Augustinegrass commercial cultivars, measured under greenhouses conditions.

| N | ENTRY | INTERNODE LENGTH | GROUP |
|---|---|---|---|
| 1 | 'Captiva' | 29.7 | f |
| 2 | 'CitraBlue' | 30.1 | f |
| 3 | 'Floratam' | 63.9 | bc |
| 4 | 'Palmetto' | 47.7 | e |
| 5 | 'Raleigh' | 67.4 | abc |
| 6 | 'Seville' | 43.5 | e |
| 7 | 'XSA 11377' | 50.8 | de |
| 8 | 'TamStar' | 58.5 | cd |
| 9 | 'Texas Common' | 67.8 | ab |

TABLE 2

Internode diameter (mm) of St. Augustinegrass commercial cultivars, measured under greenhouses conditions.

| N | ENTRY | INTERNODE DIAMETER | GROUP |
|---|---|---|---|
| 1 | 'Captiva' | 2.2 | e |
| 2 | 'CitraBlue' | 4.3 | a |
| 3 | 'Floratam' | 3.5 | b |
| 4 | 'Palmetto' | 2.6 | d |
| 5 | 'Raleigh' | 2.7 | d |
| 6 | 'Seville' | 2.8 | cd |
| 7 | 'XSA 11377' | 2.5 | de |
| 8 | 'TamStar' | 3.2 | b |
| 9 | 'Texas Common' | 2.5 | de |

TABLE 3

Node diameter (mm) of St. Augustinegrass commercial cultivars, measured under greenhouses conditions.

| N | ENTRY | NODE DIAMETER | GROUP |
|---|---|---|---|
| 1 | 'Captiva' | 4.4 | de |
| 2 | 'CitraBlue' | 6.4 | a |
| 3 | 'Floratam' | 5.0 | bcd |
| 4 | 'Palmetto' | 4.0 | e |
| 5 | 'Raleigh' | 5.3 | b |
| 6 | 'Seville' | 4.7 | bcd |
| 7 | 'XSA 11377' | 4.4 | de |
| 8 | 'TamStar' | 5.1 | bc |
| 9 | 'Texas Common' | 4.5 | cde |

TABLE 4

Leaf blade length (mm) of St. Augustinegrass commercial cultivars, measured under greenhouses conditions.

| N | ENTRY | LEAF BLADE LENGTH | GROUP |
|---|---|---|---|
| 1 | 'Captiva' | 23.2 | e |
| 2 | 'CitraBlue' | 28.7 | de |
| 3 | 'Floratam' | 34.9 | bcd |
| 4 | 'Palmetto' | 37.8 | b |
| 5 | 'Raleigh' | 39.0 | b |
| 6 | 'Seville' | 37.0 | bc |
| 7 | 'XSA 11377' | 30.0 | cde |
| 8 | 'TamStar' | 59.7 | a |
| 9 | 'Texas Common' | 38.2 | b |

TABLE 5

Leaf blade width (mm) of St. Augustinegrass commercial cultivars, measured under greenhouses conditions.

| N | ENTRY | LEAF BLADE WIDTH | GROUP |
|---|---|---|---|
| 1 | 'Captiva' | 4.5 | d |
| 2 | 'CitraBlue' | 7.6 | a |
| 3 | 'Floratam' | 7.2 | a |
| 4 | 'Palmetto' | 5.9 | bc |
| 5 | 'Raleigh' | 7.6 | a |
| 6 | 'Seville' | 5.7 | c |
| 7 | 'XSA 11377' | 7.0 | ab |
| 8 | 'TamStar' | 7.9 | a |
| 9 | 'Texas Common' | 6.1 | bc |

TABLE 6

First apical leaf length (mm) of St. Augustinegrass commercial cultivars, measured under greenhouses conditions.

| N | ENTRY | FIRST APICAL LEAF | GROUP |
|---|---|---|---|
| 1 | 'Captiva' | 30.8 | d |
| 2 | 'CitraBlue' | 29.6 | d |
| 3 | 'Floratam' | 60.4 | b |
| 4 | 'Palmetto' | 31.5 | d |
| 5 | 'Raleigh' | 36.6 | cd |
| 6 | 'Seville' | 31.1 | d |
| 7 | 'XSA 11377' | 29.9 | d |
| 8 | 'TamStar' | 77.2 | a |
| 9 | 'Texas Common' | 43.1 | C |

2016 Advanced Trial: The 2016 St. Augustinegrass Advanced Trial (16 SAT) was established in June of 2016 in three locations: Raleigh, Jackson Springs, and Laurel Springs, North Carolina (NC). Entries were planted in 3×3 ft plots with 1.5 ft alleys between entries in a Randomized Complete Block Design with three replications. Plots were evaluated 2016-2018 for establishment rate (0-100%), turf quality parameters (overall turfgrass quality, genetic color, leaf texture, density, uniformity—all rated on a scale 1-9 where 9=best), winterkill (rated on a scale 1-9 where 1=dead turf and 9=green, healthy turf), and response to any prevalent pests following National Turfgrass Evaluation Program (NTEP) guidelines (Morris and Shearman, 1998). Additionally, at Jackson Springs, NC, where sandy soils allow for the generation of drought conditions with relative ease, plots were evaluated for drought tolerance by cutting irrigation off during periods when no rain was forecasted and rating leaf firing (on a scale of 1-9 where 1=dead turf and 9=green, healthy turf). Epidemics of gray leaf spot (caused by *Pyricularia grisea*) occurred in Laurel Springs and Jackson Springs, NC in 2016, while an infestation of the southern chinch bug (*Blissus insularis*) was present in Jackson Springs, NC in 2018. Data on overall turf quality, final establishment in year 1 (a measure of a line's aggressiveness), gray leaf spot tolerance (0-100% where 100% severe disease) and southern chinch bug tolerance (rated 1-9) where 9=no damage) is presented in FIGS. 6A-6D. 'XSA 11377' was the top performer in terms of establishment, drought tolerance and chinch bug tolerance. Furthermore, the cultivar was among the top performers for turfgrass quality and gray leaf spot tolerance. 'XSA 11377' outperformed the commercial cultivars for each of these tested traits.

Farm Trials: The best 2-3 lines from each the 2014, 2015, and 2016 Advanced Trials, including 'XSA 11377', were advanced to St. Augustinegrass On-Farm Trials (SOFT). Eight NC State (NCSU) lines, eight University of Florida (UF) lines, and commercial checks 'Raleigh', 'Palmetto', and 'CitraBlue' were established at sites at Jackson Springs, NC and Crosby, Texas (TX) in June of 2017. An additional copy of the trial was planted at Burgaw, NC, in July of 2018. Entries were planted in 5×5 ft plots with 1.5 ft alleys between entries in a Randomized Complete Block Design with three replications.

Figure 8:
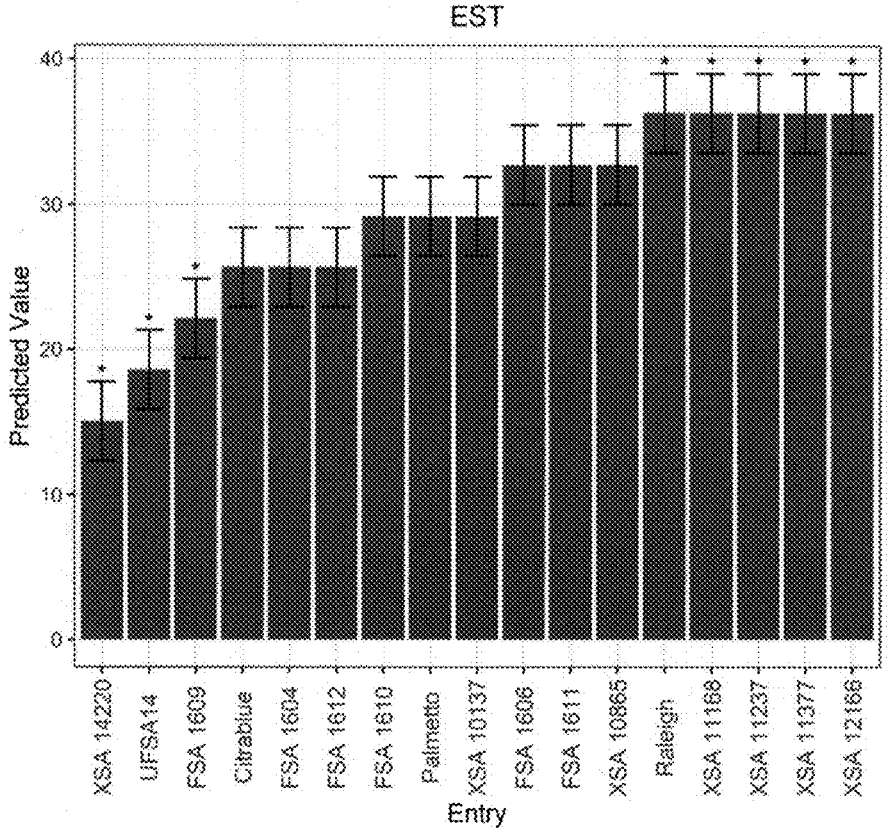
FIG. 8 shows images of bar graphs from analyses of Best linear unbiased predictor (BLUP) values of St. Augustinegrass breeding lines and commercial checks evaluated 2017-2019 at the Jackson Springs, NC site for establishment rate (EST), turf quality (TQ), gray leaf spot incidence (GLS), fall color (FC), winterkill (WK), and drought tolerance (Drought). * denotes genotypes that significantly outperformed the mean at 5% probability by Student's t-test.
Figure 8:
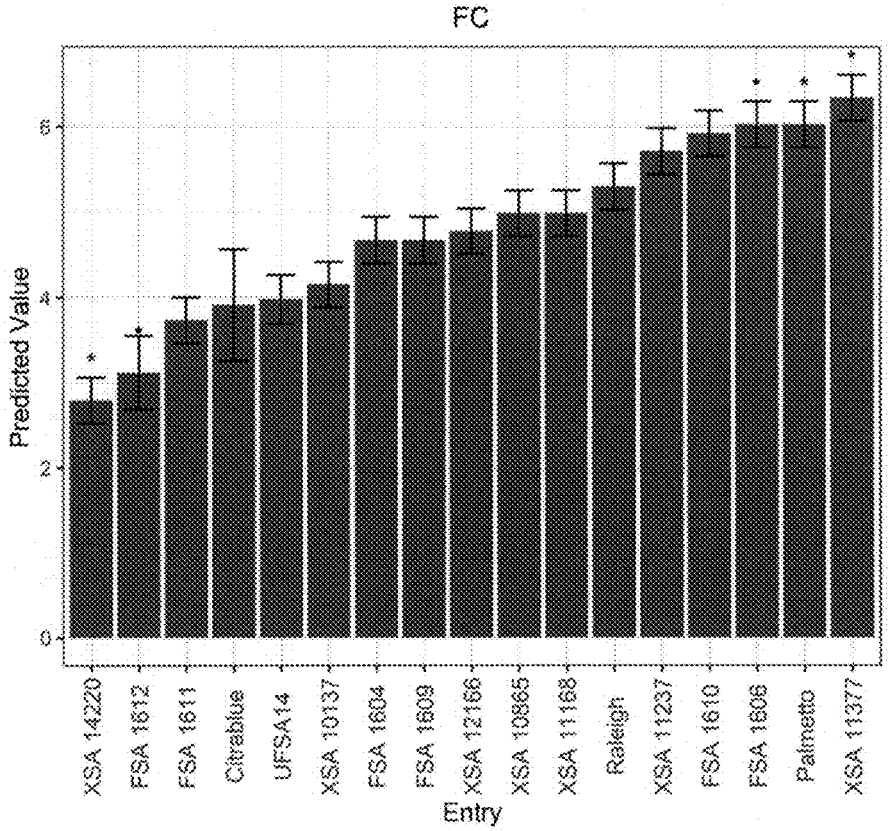
Figure 8:
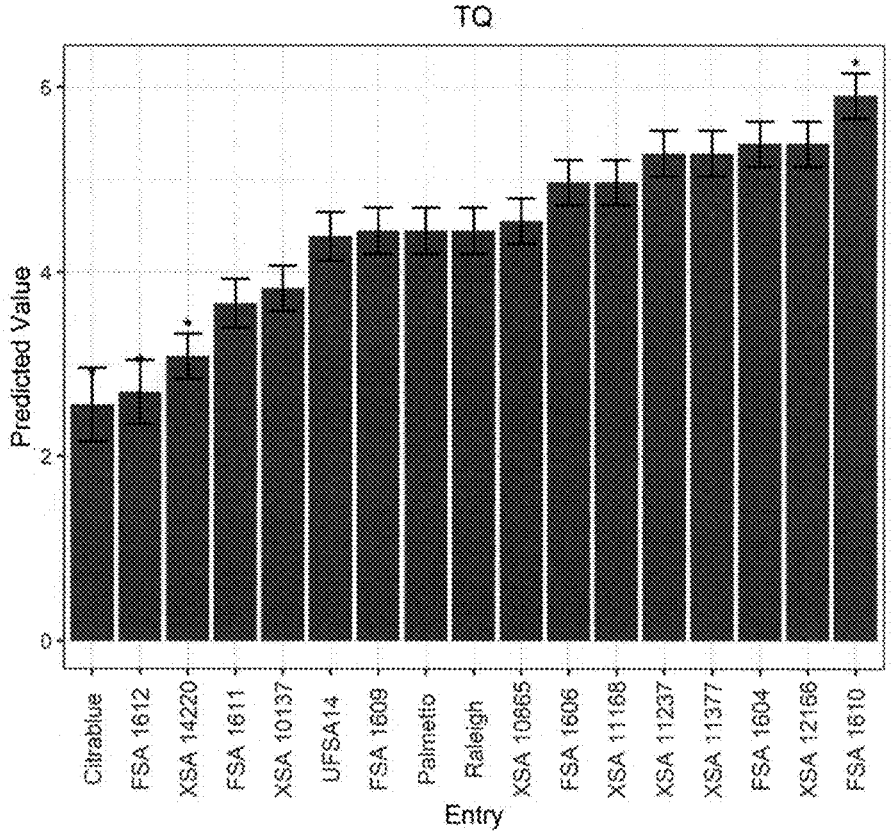
Figure 8:
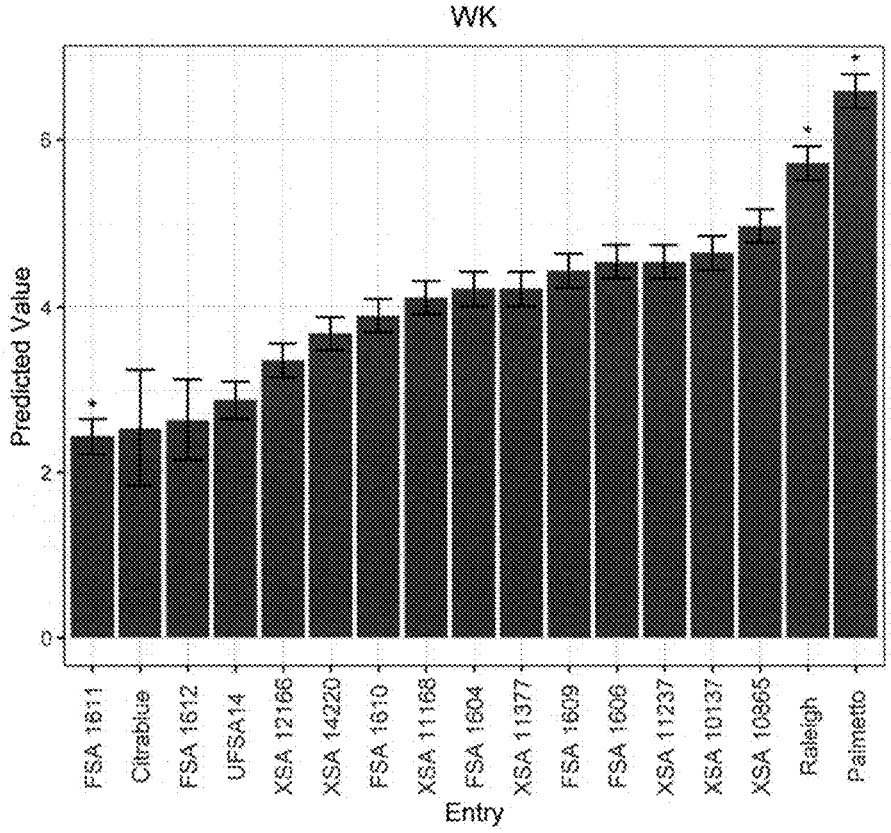
Figure 8:
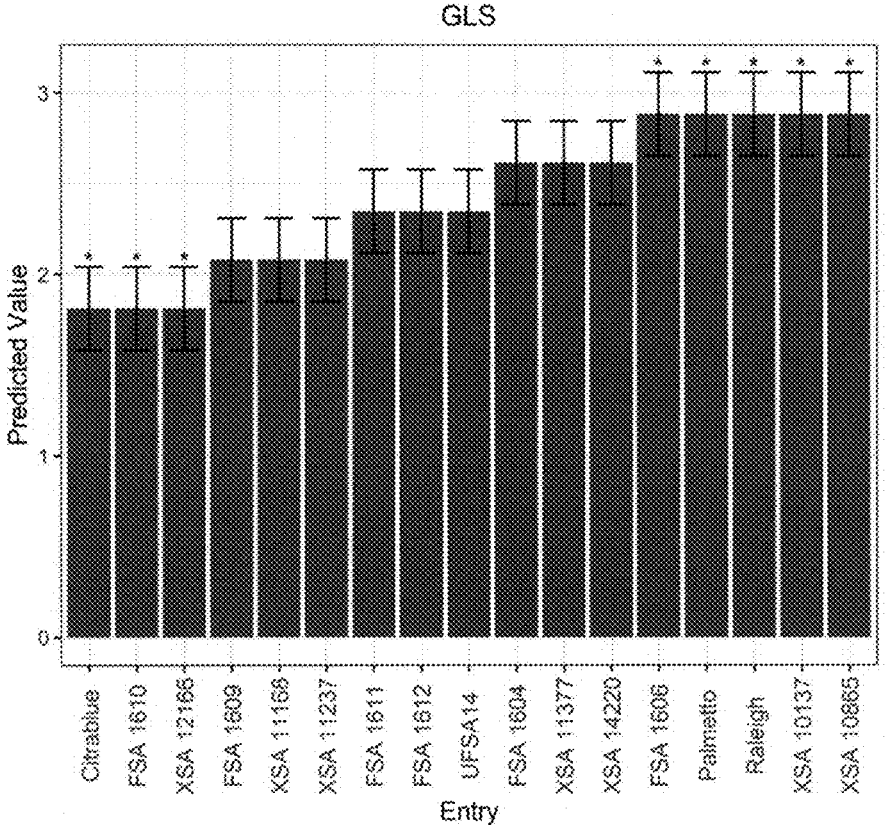
Figure 8:
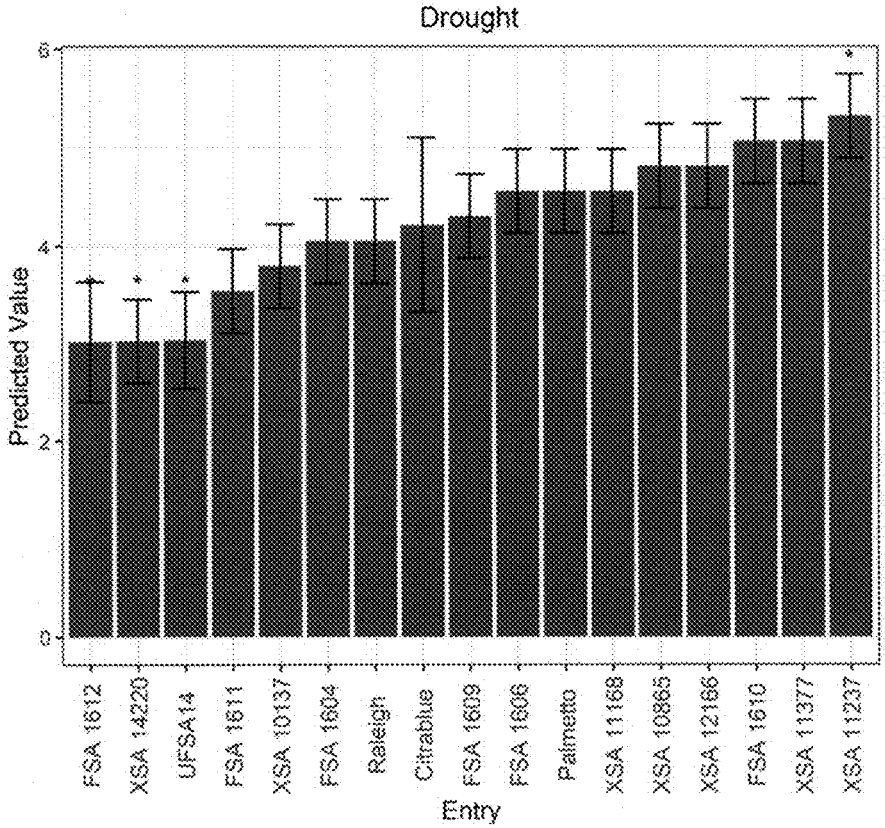

2017 Jackson Springs, NC SOFT: The 17 Jackson Springs NC SOFT was evaluated 2017-2019 for establishment rate, turf quality parameters (overall turf quality, genetic color, leaf texture, density and uniformity), winterkill, drought tolerance, fall color and response to any prevalent pests following National Turfgrass Evaluation Program (NTEP) guidelines. A late frost in May of 2018 following partial green up of the plots, caused severe winterkill on most entries. However, except for a few UF lines, most plots made a full recovery by summer of that year. No SCB infestations occurred during the life of the trial and only modest GLS incidence was observed in 2018. 'XSA 11377' significantly (p=0.05) outperformed the mean of all entries in terms of establishment rate and fall color (FIG. 8). Additionally, it was numerically superior to all checks in EST, turf quality, fall color and drought tolerance.

Figure 9:
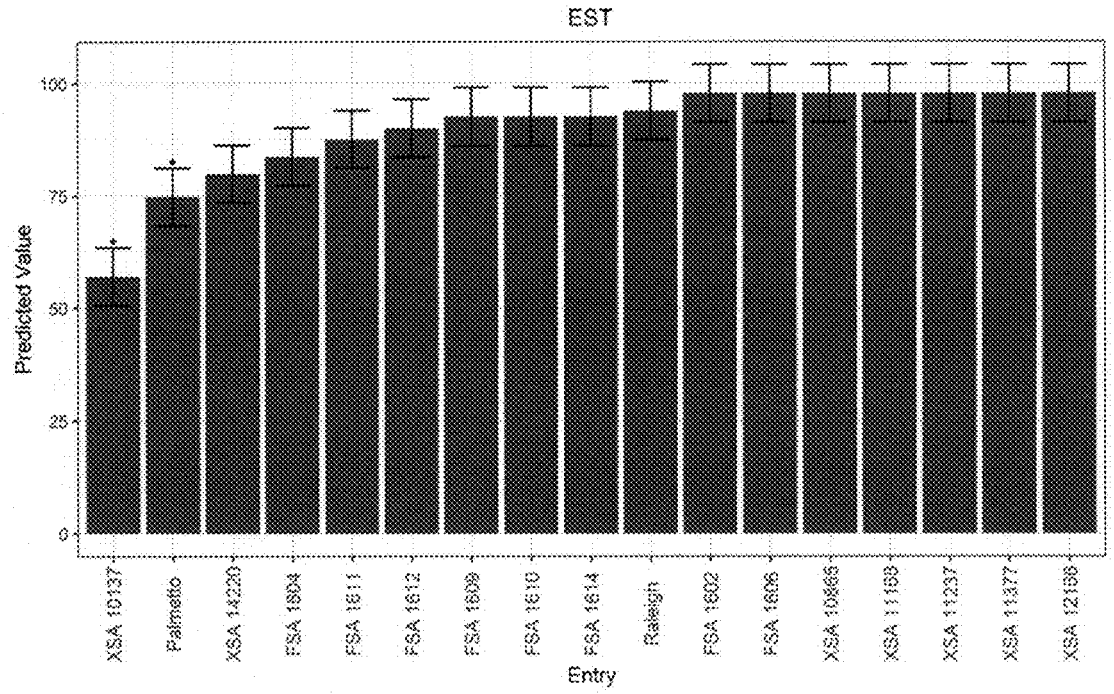
FIG. 9 shows images of bar graphs from analyses of BLUP values for St. Augustinegrass breeding lines and commercial checks evaluated 2017-2019 at the Crosby, TX site for establishment (EST), turf quality (TQ), and genetic color (Color). * denotes genotypes that significantly outperformed the mean at 5% probability by t-Student test.
Figure 9:
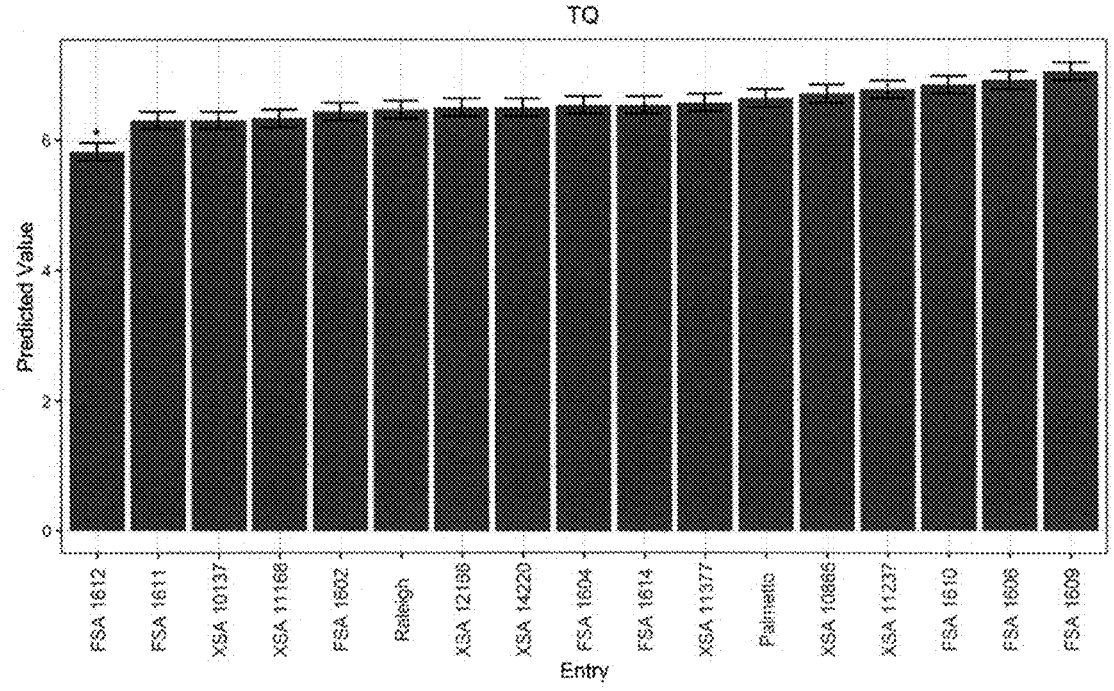
Figure 9:
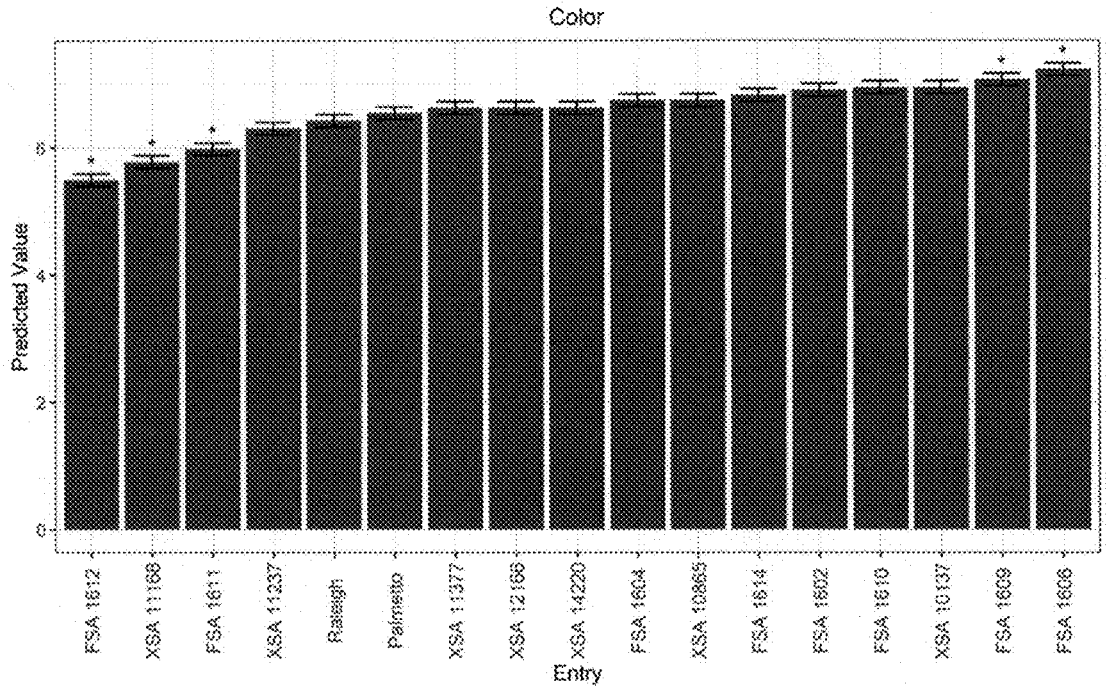

2017 Crosby, TX SOFT: The trial was evaluated for establishment rate (EST) at the end of year 1, and turf quality and genetic color at the peak of season 2017-2018. 'XSA 11377' reached higher establishment than the checks at the end of year 1. The line was comparable to the checks in terms of TQ and Color (FIG. 9).

Figure 10:
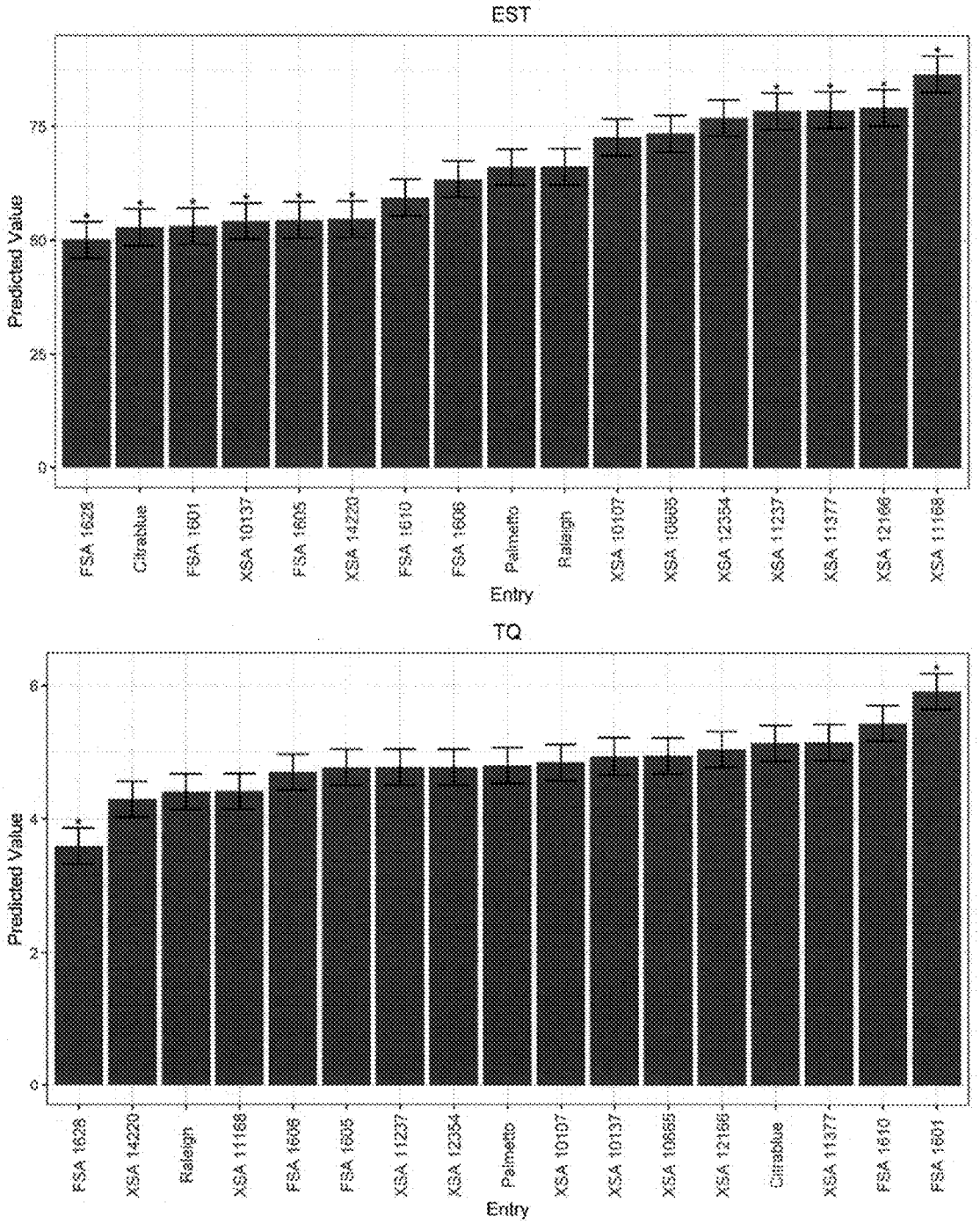
FIG. 10 shows images of bar graphs from analyses of BLUP values for St. Augustinegrass breeding lines by modified base index, and commercial checks evaluated 2018-2019 at the Burgaw, NC site for establishment (EST), percent green cover (PGC), turf quality (TQ), winterkill (WK), fall color (FC), drought tolerance (Drought), gray leaf spot incidence (GLS), and southern chinch bug incidence (SCB) . * denotes genotypes that significantly outperformed the mean at 5% probability by Student's t-test.
Figure 10:
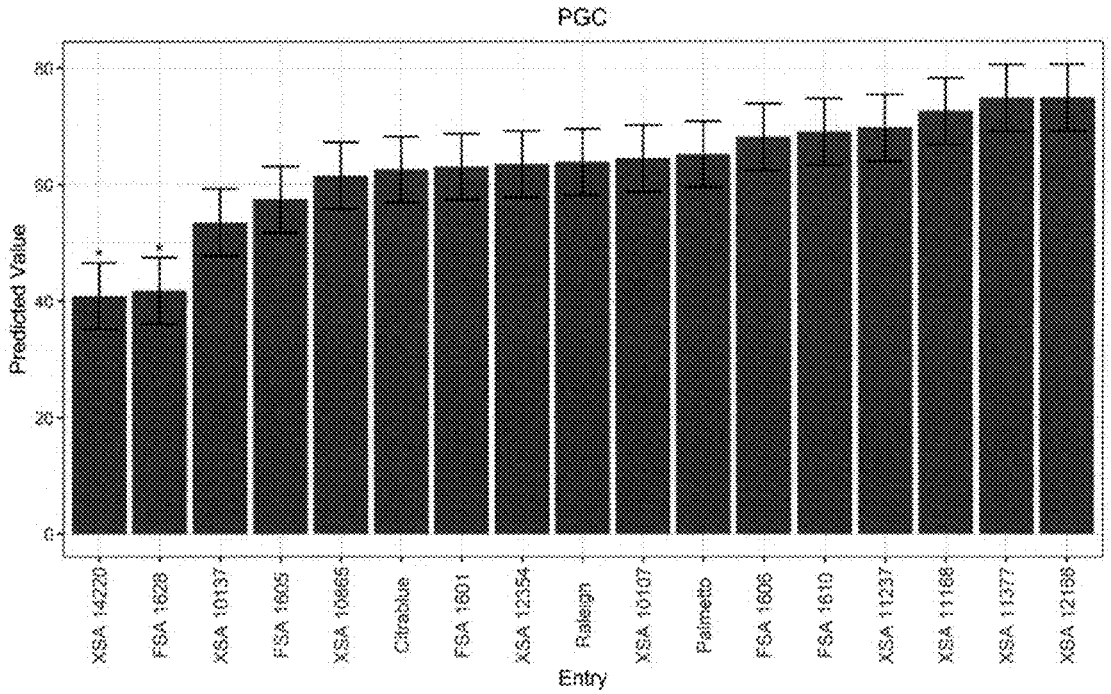
Figure 10:
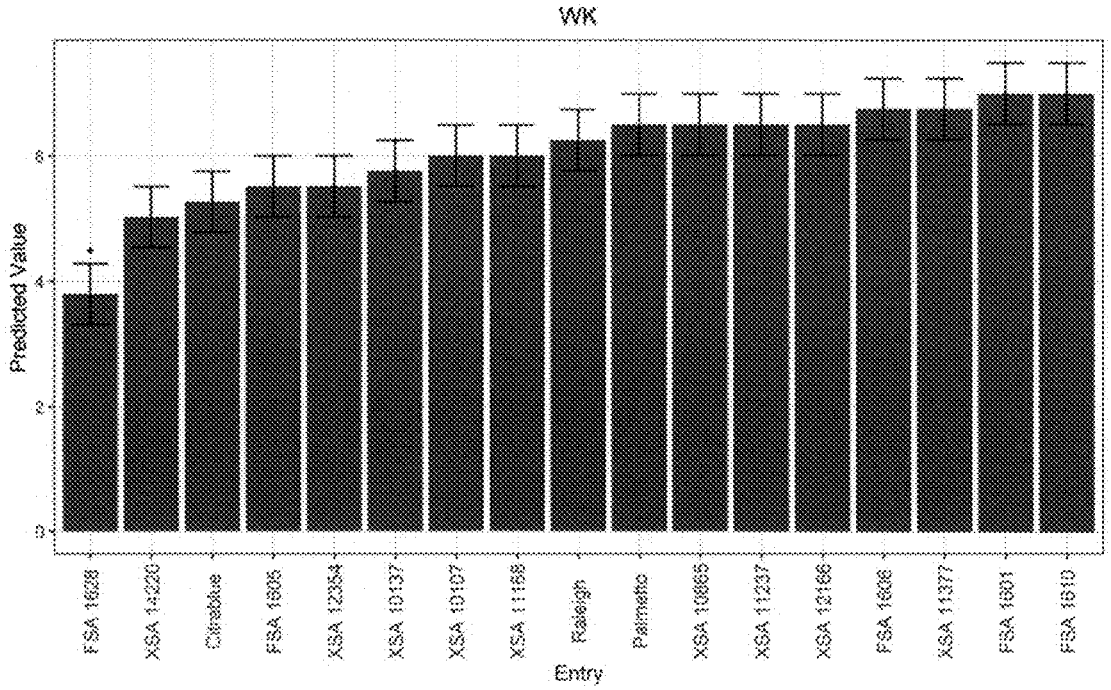
Figure 10:
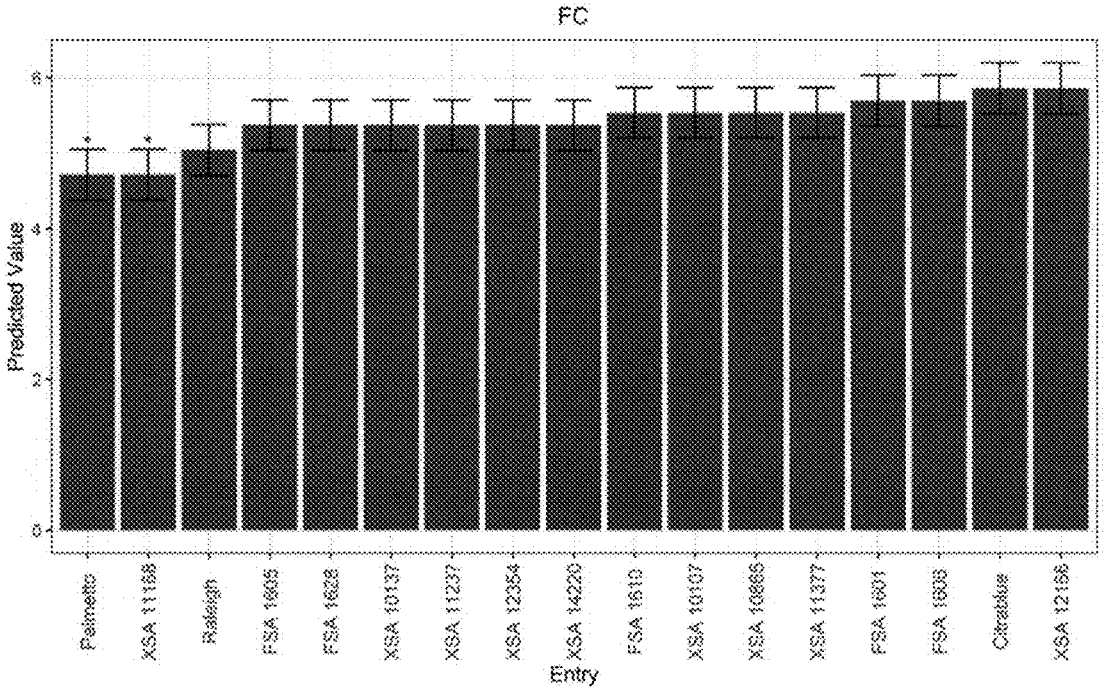
Figure 10:
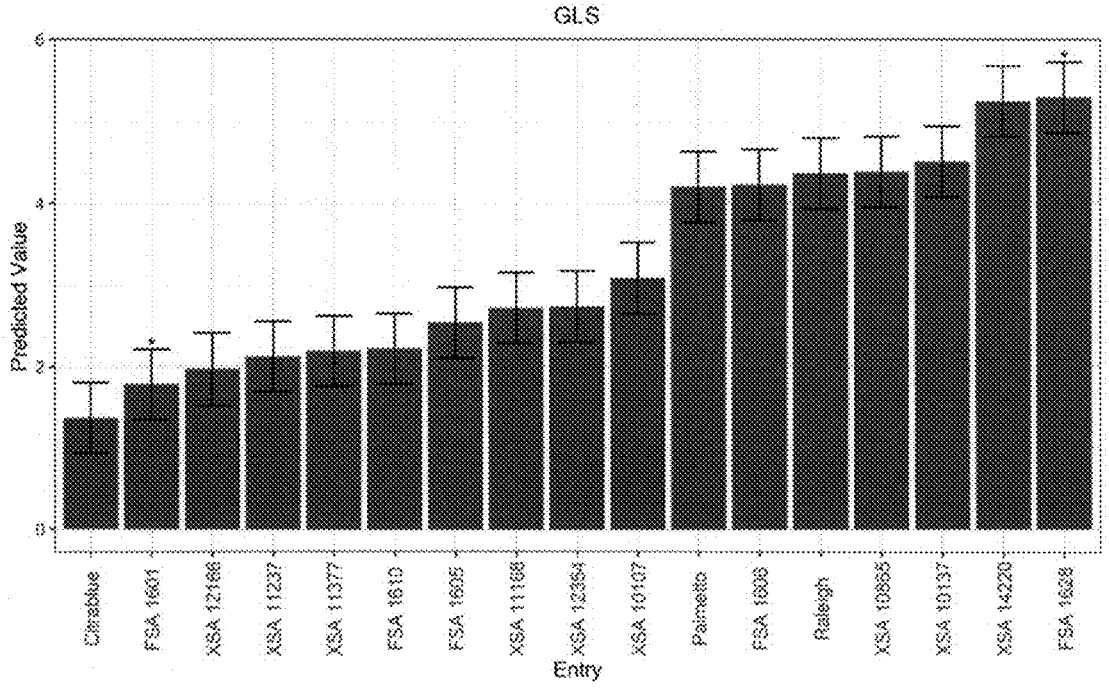
Figure 10:
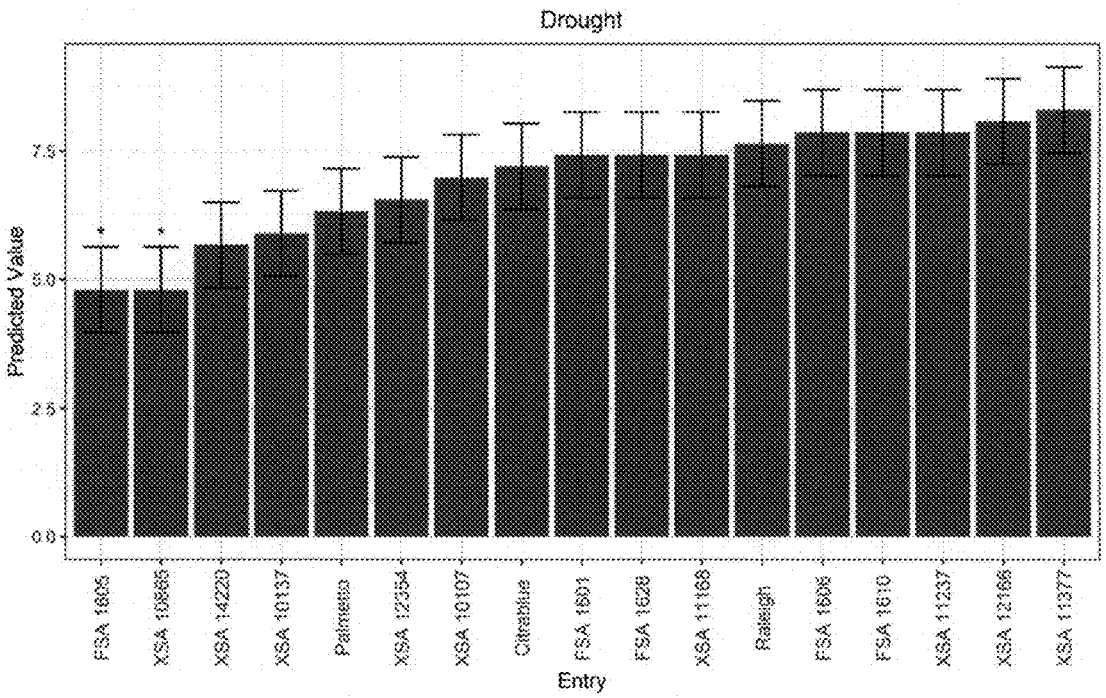
Figure 10:
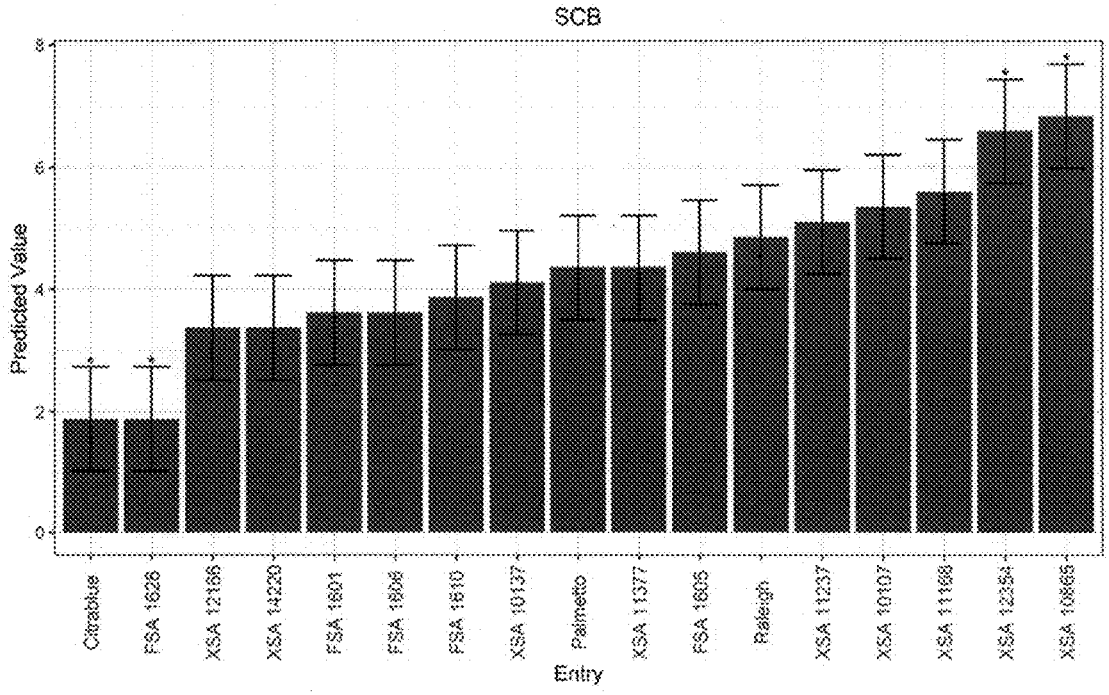

2018 Burgaw, NC SOFT. This trial was of interest because environmental conditions (soil type, humidity and temperature) at this site are conducive for heavy gray leaf spot and southern chinch bug infestations. Severe epidemics of both of these pest occurred in 2019. Because of severe plot loss for some of the entries, the plots were evaluated for final percent cover as a measure of overall stress tolerance and persistence. At this site, 'XSA 11377' significantly (p=0.05) outperformed the mean in establishment rate. It was the best line in drought tolerance, third in winterkill, and fourth in fall color. While 'XSA 11377' is not completely resistant to chinch bugs and gray leaf spot, it outperformed both 'Raleigh' and 'Seville' for the second, and 'Raleigh' for the first. Furthermore, under such high incidence of both pathogens, 'XSA 11377' ranked second in percent green cover at the end of the year and third in overall turf quality across years of evaluation (FIG. 10).

Figure 11:
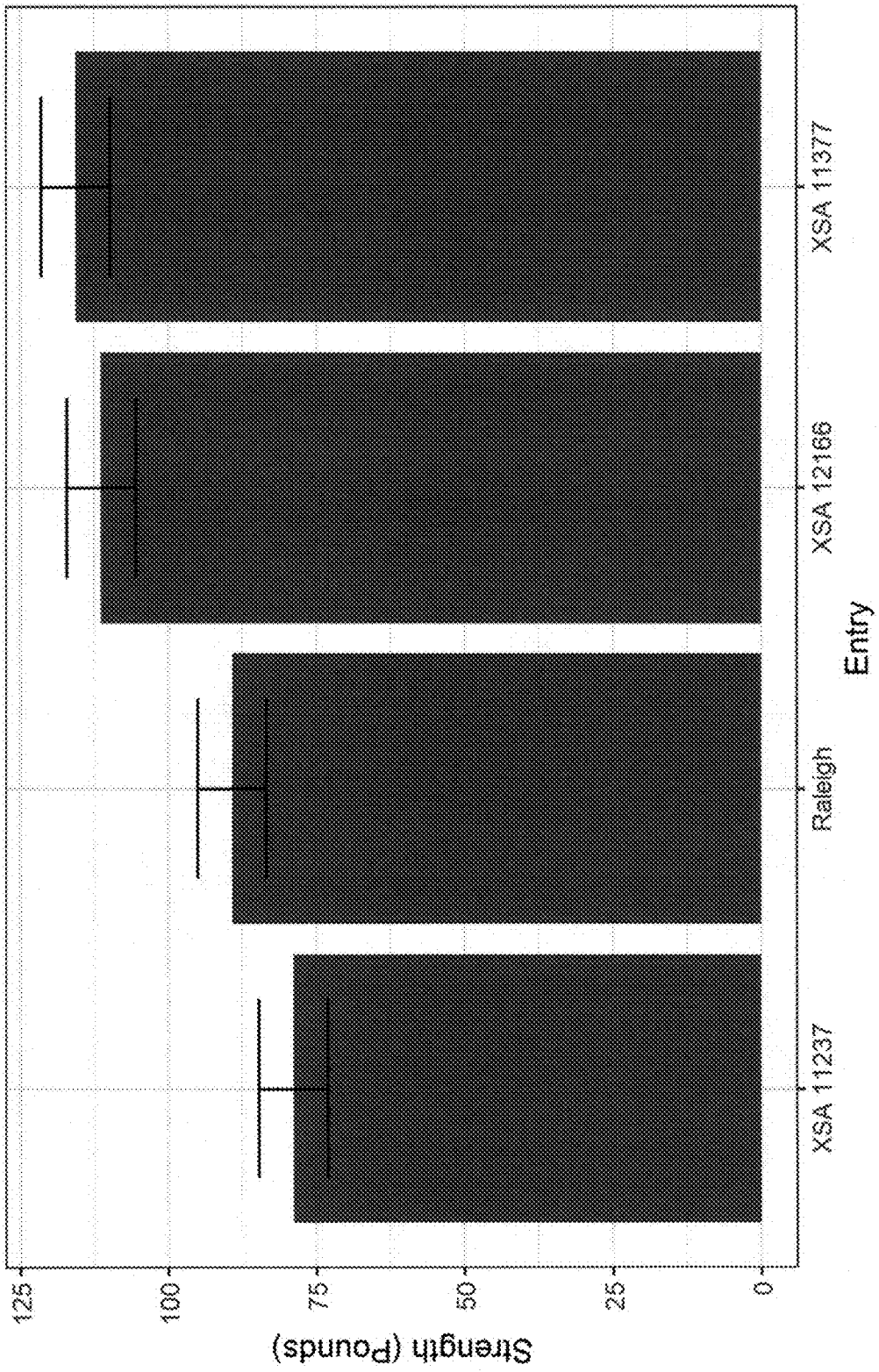
FIG. 11 shows an image of a bar graph from analyses of least squares (LS) means across ten measurements of sod tensile strength (measured as the peak fore required to tear the sod slab using a hand winch and force transducer/recorder system) in each of three replications at Burgaw, NC. Commercial cultivar 'Raleigh' was included as a control comparison ("check").

Production Trials: In August 2019, the best four performing lines in the SOFT trials and cultivar 'Raleigh' were planted in 8×12 ft strips at Burgaw, NC and Crosby, TX to evaluate sod production traits. At Burgaw, NC, three sod strips 12 inches in width and 20 ft in length were mechanically harvested using commercial equipment. Each strip was then cut into 18-inch pieces. Each of 10 sod slabs per strip were evaluated for sod tensile strength. The tensile strength was measured as the peak force required to tear the sod slab using a hand winch and force transducer/recorder system (Jha. 2018). 'XSA 11377' was in the top group of performance and was significantly (p=0.05) better than 'Raleigh' (FIG. 11).

At the Crosby TX site, 10 sod pieces 12 inches in width and 18 inches in length were mechanically harvested using commercial equipment. Tensile strength was evaluated by lifting the sod pieces by a corner and rating their ability to stay intact on a scale of 1-9 (1=poor and 9=excellent) per NTEP guidelines. Means across samples are presented in Table 7.

Figure 12:
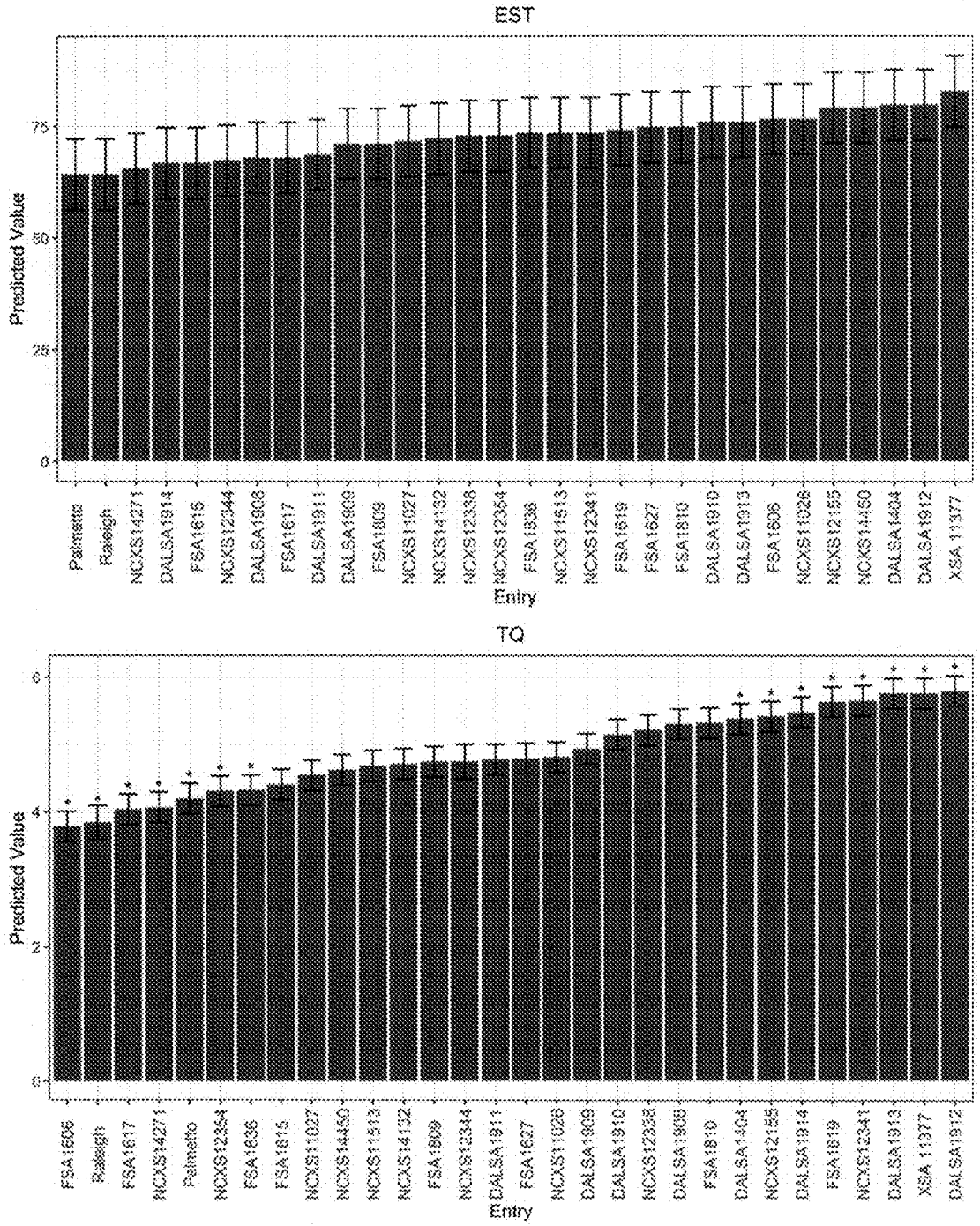
FIG. 12 shows images of bar graphs from analyses of predicted values of St. Augustinegrass breeding lines by modified base index, and commercial checks evaluated 2020-2021 under 63% shade in Raleigh, NC for EST=establishment, PGC=percent green cover, and TQ=turf quality. * denotes genotypes that significantly outperformed the mean at 5% probability by t-Student test.
Figure 12:
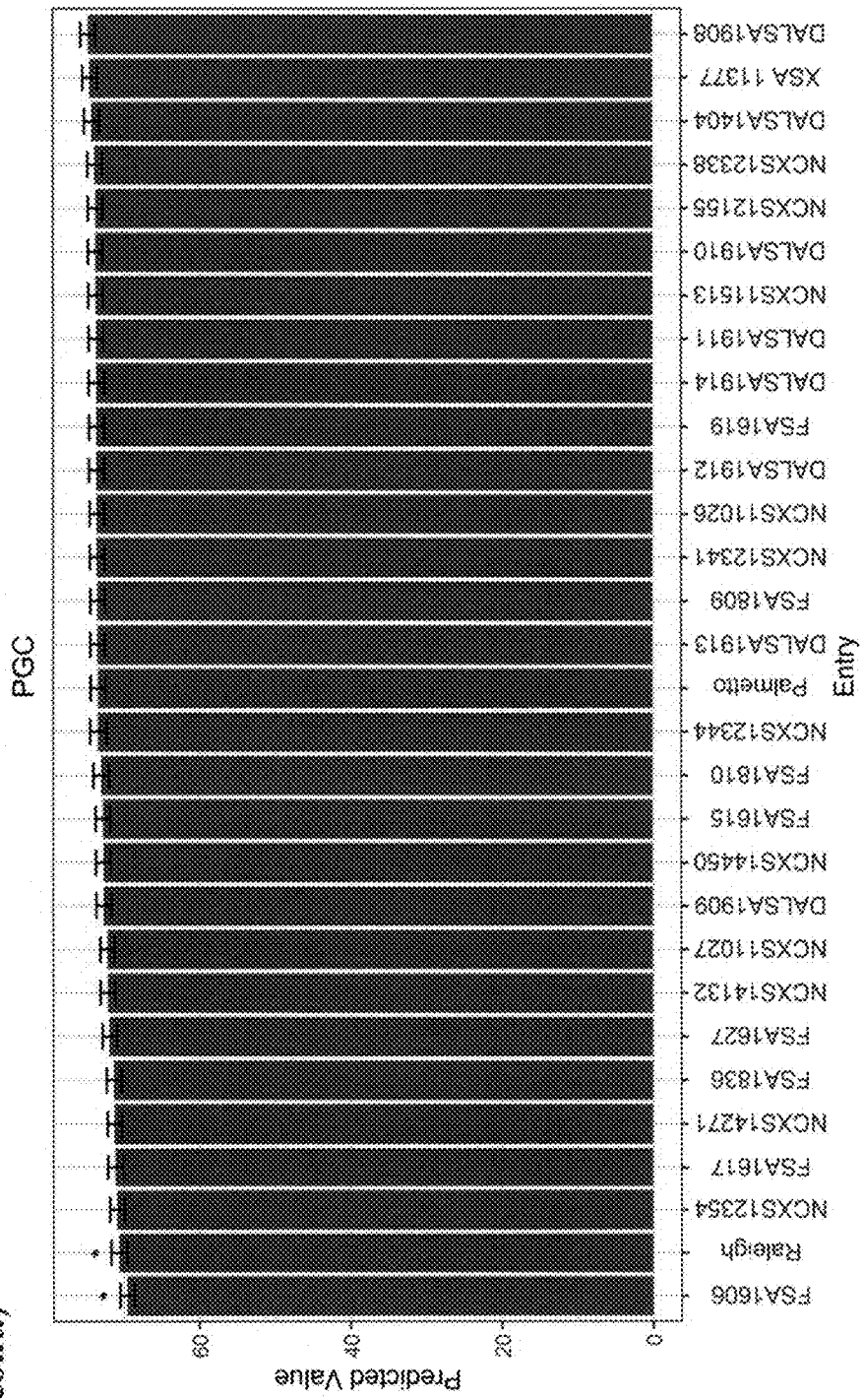

Shade Trial. A shade trial was established at the Raleigh, NC site in summer 2020. The trial was planted under a structure fitted with a 63% shade cloth. Eleven breeding lines from the NC State (NCSU) turfgrass breeding program, eight from University of Florida (UF), eight from Texas A&M University (TAMU), and three controls ('Raleigh', 'Palmetto' and 'DALSA 1404') were established from 10×7 inch plugs in 9 sq ft plots in a Randomized Complete Block Design with three replications. The trial was evaluated 2020-2021 for establishment rate (EST), percent green cover (PGC), and turf quality (TQ) all under shade. 'XSA 11377' exhibited superior performance under shade, significantly (p=0.05) outperforming the mean for PGC and TQ (FIG. 12). Furthermore, 'XSA 11377' ranked first for EST and TQ, and second for PGC.

Figure 13A:
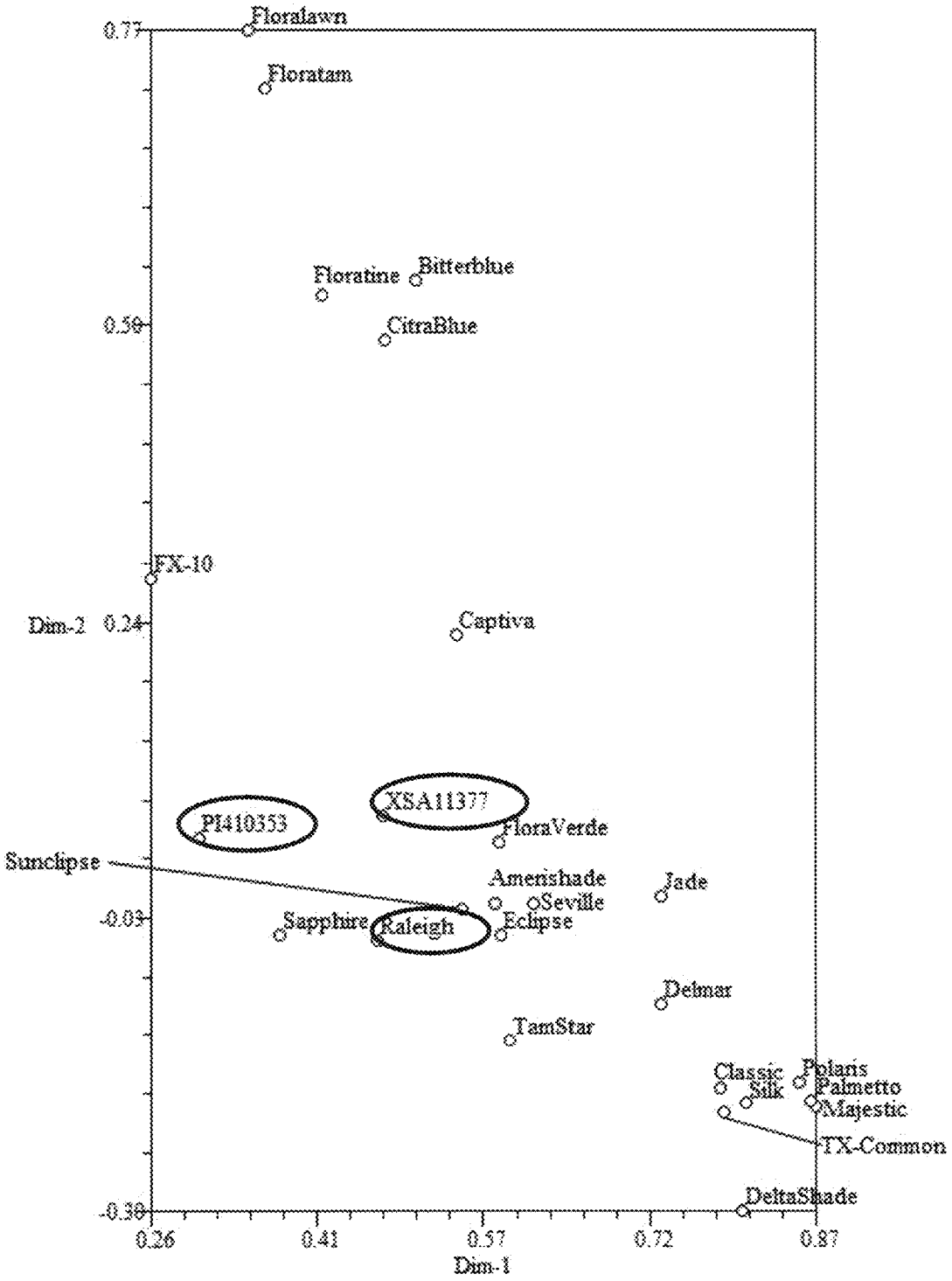
FIGS. 13A-13B show images of Principal Coordinate (PCO) analysis 2D (FIG. 13A) and 3D (FIG. 13B) plots of 24 St. Augustinegrass commercial cultivars and 'XSA 11377' generated using 134 Simple Sequence Repeat alleles. 'XSA 11377' and its two parents are circled.
Figure 13B:
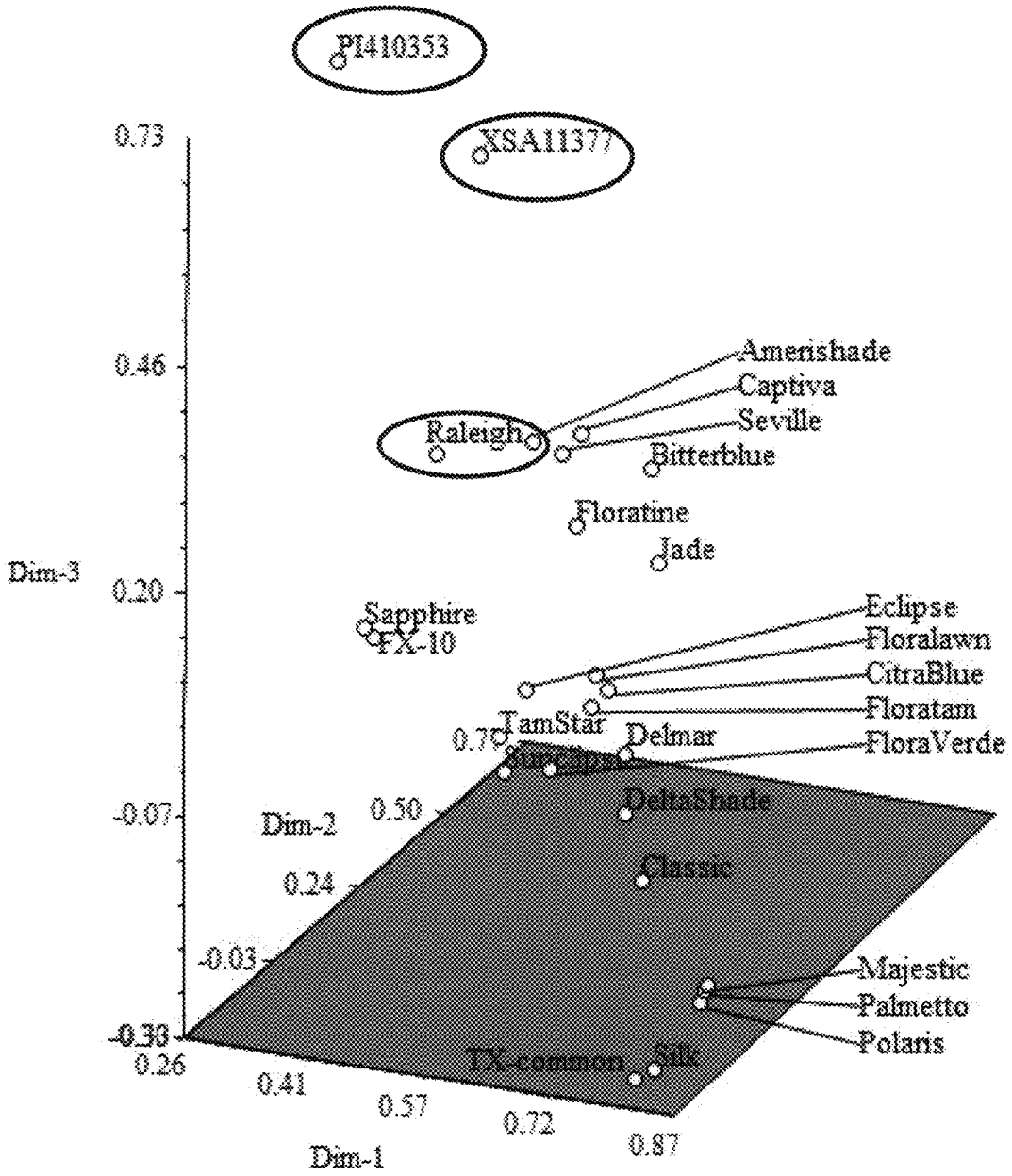
Figure 14A:
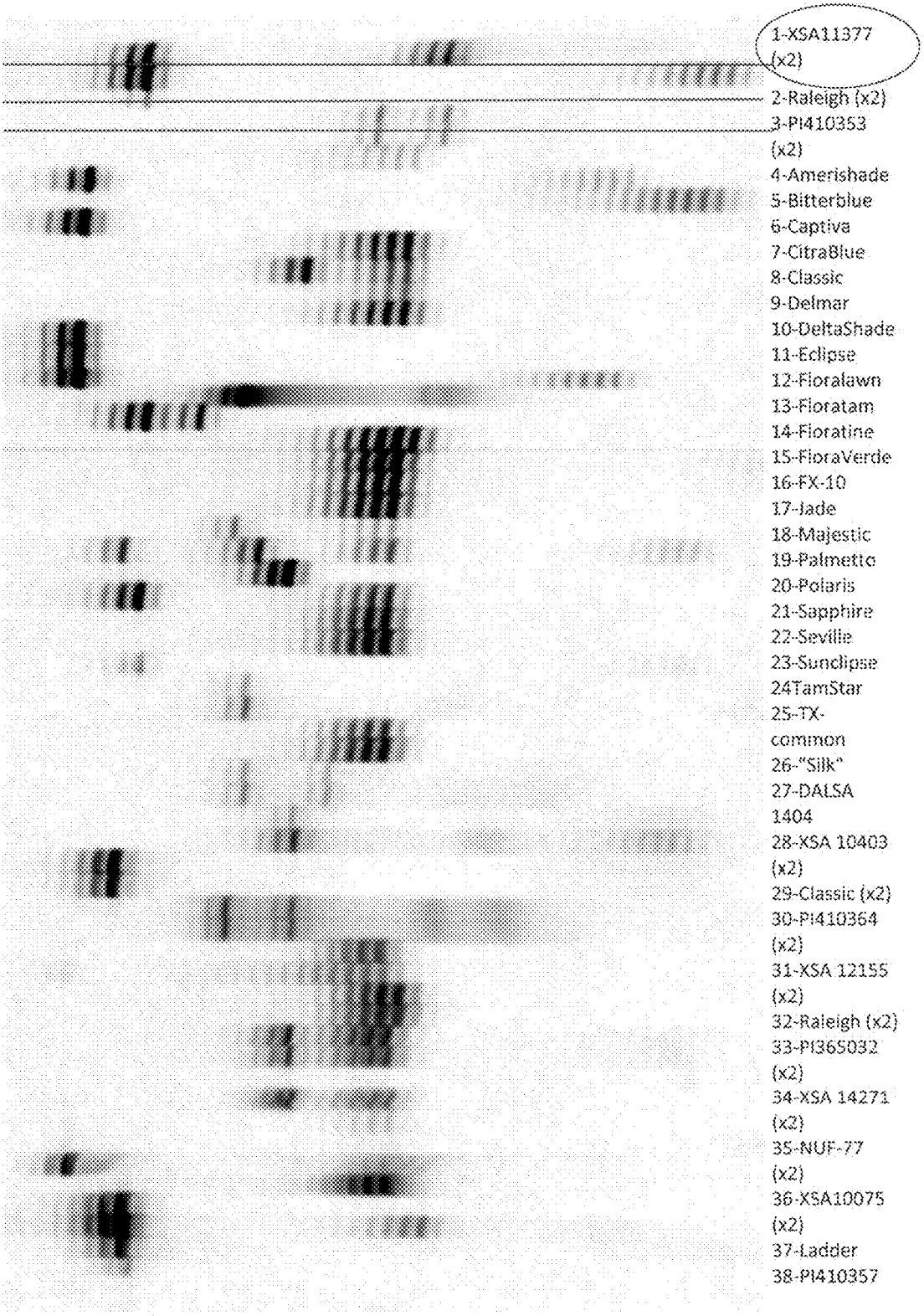
FIGS. 14A-14B show image of gels displaying results of PCR amplification of 24 St. Augustinegrass commercial cultivars and 'XSA 11377' with simple sequence repeat primer pair 17792 (FIG. 14B) or simple sequence repeat primer pair 29269 (FIG. 14B).
Figure 14B:
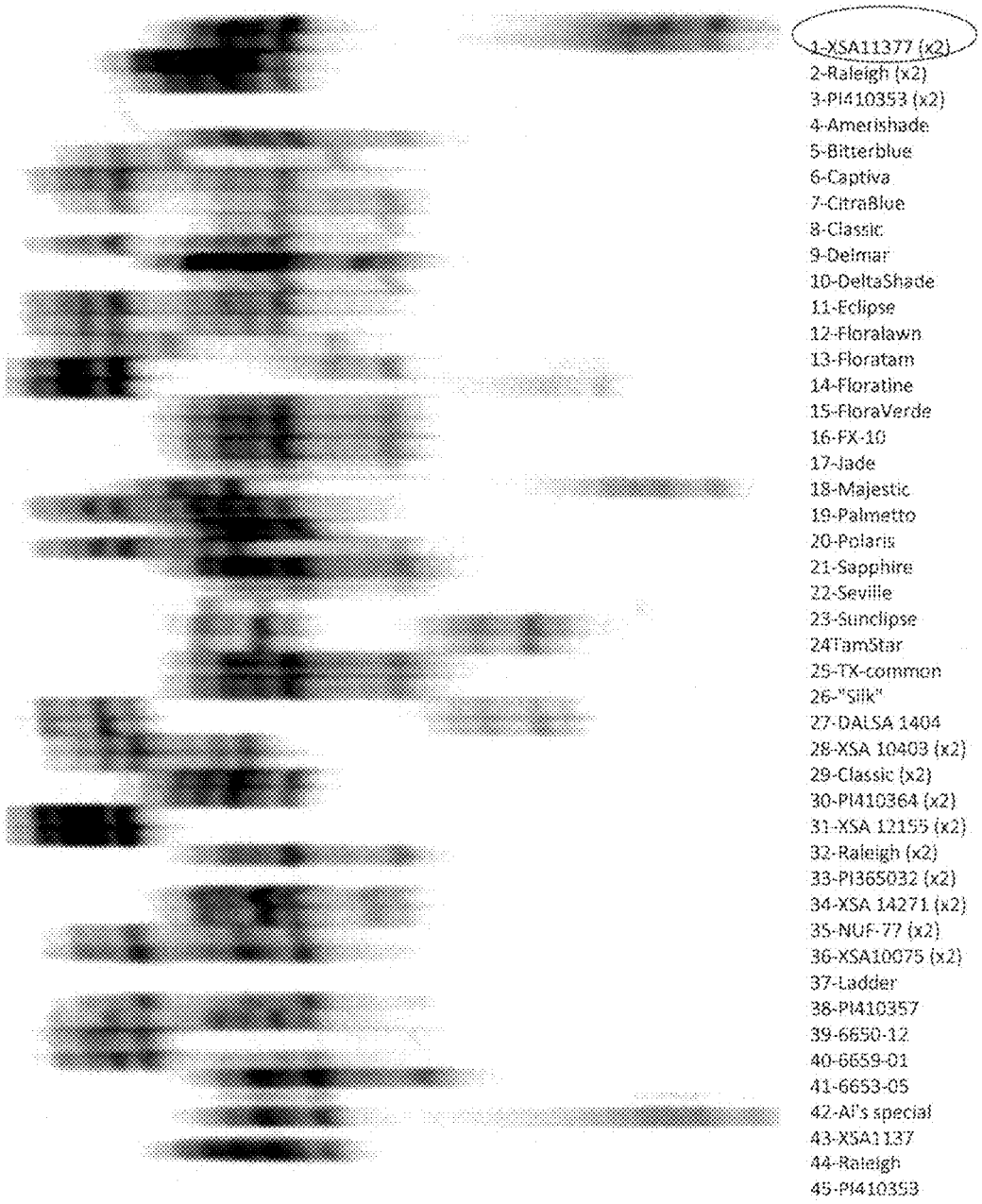

DNA Fingerprinting. In order to demonstrate that 'XSA 11377' is a unique genotype and genetically different from all major St. Augustinegrass cultivars currently on the market known to the Inventor, simple sequence repeat (SSR) markers were used to generate DNA fingerprints of these materials. Twenty three commercial cultivars (Table 8). 'XSA 11377' and its two parents, cultivar 'Raleigh' (female parent) and PI 410353 (male parent), were genotyped with 16 SSR primer pairs (Table 9) developed by Mulkey et al. (2014). A total of 16 loci were amplified (one locus per primer pair). The number of alleles per locus ranged between 5 and 13 for a total of 134 alleles analyzed (Table 9). Levels of polymorphism among the materials analyzed were comparable to those found in previous studies (Milla-Lewis et al., 2013; Mulkey et al, 2013; 2014). Genetic similarity values were calculated for all pairwise genotype combinations according to Dice (1945) using NTSYSpc v 2.2. (Rohlf, 2000). Dice similarities were then used to construct a dendrogram using the UPGMA (Sokal and Michener, 1958) clustering procedure in order to assess genetic relationships among genotypes. Additionally, a principal coordinate analysis (PCO) was performed for the same purpose. Both the dendrogram and the PCO plots (FIGS. 13A-13B) showed clear separation between 'XSA 11377' and all other commercial cultivars currently in the market known to the Inventor, indicating the genetic distinctness of this line. Furthermore, only one SSR primer was sufficient to separate 'XSA 11377' from all other cultivars tested. Examples of this are SSR profiles of primer 17792 (FIG. 14A) and primer 29269 (FIG. 14B). The SSR data presented here further indicates that 'XSA 11377' is a unique genotype.

Based on available data, 'XSA 11377' is unique not only because SSR data shows it is genetically distinct from all major St. Augustinegrass cultivars currently on the market known to the Inventor, but also because it is fast to establish, has good levels of shade and drought tolerances, and has superior turf quality over the cultivar 'Raleigh'. Furthermore, in comparison to 'Raleigh', this cultivar has slightly better gray leaf spot and chinch bug tolerance, and significantly better sod strength, traits that are desirable to reduce management costs and increase harvest ability in sod production. Overall, 'XSA 11377' maintains acceptable turf quality under normal management practices (FIGS. 6A-6C) making it a desirable grass for home lawns and landscapes in the southern US and into the transition zone. Turf quality (TQ) is based on 9 being outstanding or ideal turf and 1 being poorest or dead. A rating of 6 or above is generally considered acceptable.

TABLE 7

Data collected on slab quality for sod quality evaluations at Crosby, TX.

| Entries | Color | TQ | Tensile Strength |
|---|---|---|---|
| 'Raleigh' | 7 | 6 | 6 |
| 'XSA 11377' | 8 | 8 | 8 |

TABLE 8

List of genotypes used for comparison of genetic similarity between 'XSA 11377' and major commercial cultivars of St. Augustinegrass.

| Num. | Genotype | Source | Ploidy level |
|---|---|---|---|
| 1 | 'Raleigh' [unpatented] | NC State University | Diploid (2n = 2X = 18) |
| 2 | PI410353* | Plant Genetic Resources Conservation Unit (Griffin, GA) | Diploid (2n = 2X = 18) |
| 3 | 'Amerishade' [U.S. Plant Pat. No. 17,095 as 'TR 6-10'; marketed under tradename Amerishade ®] | Scotts ® | Diploid (2n = 2X = 18) |
| 4 | 'Bitterblue' [unpatented] | Collection from farmer's fields | Triploid (2n = 3X = 27) |
| 5 | 'Captiva' [U.S. Plant Pat. No. 21,280 as 'NUF-76'; marketed under tradename Captiva ®] | University of Florida | Diploid (2n = 2X = 18) |
| 6 | 'CitraBlue' [U.S. Plant Pat. No. 32,456 as 'FSA 1602'; marketed under tradename CitraBlue ®] | University of Florida | Tetraploid (2n = 4X = 36) |
| 7 | 'Classic' [unpatented] | Woerner Farms | Diploid (2n = 2X = 18) |
| 8 | 'Delmar' [U.S. Plant Pat. No. 6,372] | Scotts ® | Diploid (2n = 2X = 18) |
| 9 | 'DeltaShade' [unpatented] | Environmental Turf | Diploid (2n = 2X = 18) |
| 10 | 'Eclipse' [U.S. Plant Pat. No. 21,603] | Mississippi State University | Diploid (2n = 2X = 18) |
| 11 | 'Floralawn' [unpatented] | University of Florida | Triploid (2n = 3X = 32) |
| 12 | 'Floratam' [unpatented] | University of Florida | Triploid (2n = 3X = 32) |
| 13 | 'Floratine' [unpatented] | University of Florida | Triploid (2n = 3X = 27) |
| 14 | 'FloraVerde' [unpatented] | University of Florida | Diploid (2n = 2X = 18) |
| 15 | 'FX-10' [U.S. Plant Pat. No. 7,852] | University of Florida | Triploid (2n = 3X = 30) |
| 16 | 'Jade' [U.S. Plant Pat. No. 6,921 as '6-72-182'] | Scotts ® | Diploid (2n = 2X = 18) |
| 17 | 'Majestic' [unpatented] | Collection from farmer's fields | Diploid (2n = 2X = 18) |
| 18 | 'Palmetto' [U.S. Plant Pat. No. 9,395] | Sod Solutions Inc. | Diploid (2n = 2X = 18) |

TABLE 8-continued

List of genotypes used for comparison of genetic similarity between 'XSA 11377' and major commercial cultivars of St. Augustinegrass.

| Num. | Genotype | Source | Ploidy level |
|---|---|---|---|
| 19 | 'Polaris' [U.S. Plant Pat. No. 21,240] | Mississippi State University | Diploid (2n = 2X = 18) |
| 20 | 'Sapphire' [U.S. Plant Pat. No. 16,174 as 'B12'; marketed under tradename Sapphire ™] | Ozbreed Australia | Diploid (2n = 2X = 18) |
| 21 | 'Seville' [U.S. Plant Pat. No. 4,097] | Scotts ® | Diploid (2n = 2X = 18) |
| 22 | 'Sunclipse' [U.S. Plant Pat. No. 6,922 as '6-72-130'] | Scotts ® | Diploid (2n = 2X = 18) |
| 23 | 'TamStar' [U.S. Plant Pat. No. 27,393 as 'DALSA 0605'; marketed under tradename TamStar ®] | Texas AgriLife | Diploid (2n = 2X = 18) |
| 24 | 'Texas Common' [unpatented] | Collection from farmer's fields | Diploid (2n = 2X = 18) |
| 25 | 'Silk' [unpatented] | Mississippi State University | Diploid (2n = 2X = 18) |

*Although not a cultivar, plant introduction 410353 was included in the analysis because it is the male parent of 'XSA 11377'.

TABLE 9

Summary statistics for Simple Sequence Repeat primers used to assess genetic relatedness among 'XSA 11377' and St. Augustinegrass commercial cultivars.

| Primer Pair No. | Primer Name | No. of alleles amplified | Primer Sequence |
|---|---|---|---|
| 1 | 1646 | 12 | F (SEQ ID NO: 1): TTCATCTGTTGCCAATATACATCA<br>R (SEQ ID NO: 2): GGGTAGGAATGAGGAATCCAA |
| 2 | 1709 | 6 | F (SEQ ID NO: 3): CTCGCGCCAAAGAAGAGG<br>R (SEQ ID NO: 4): CCCGGGCTTGAATTGAC |
| 3 | 2503 | 9 | F (SEQ ID NO: 5): ACCTGGTACTGCAACCGTCT<br>R (SEQ ID NO: 6): TCTCTCTAGTCTCTCTGAACTGAGC |
| 4 | 17792 | 13 | F (SEQ ID NO: 7): TCCTACAAGACAATCAAATCTGGA<br>R (SEQ ID NO: 8): GGGCACACAATTGAGTTCAGTA |
| 5 | 23060 | 7 | F (SEQ ID NO: 9): GGCCTCCGACGAGGAATA<br>R (SEQ ID NO: 10): ACTAGATCCACGGAGCAGGA |
| 6 | 23965 | 8 | F (SEQ ID NO: 11): CACGAGGCTGTACTACCACTCA<br>R (SEQ ID NO: 12): TGAAATGTTAAGTTTGTGCGTGT |
| 7 | 27477 | 9 | F (SEQ ID NO: 13): GAGTGCTAGGCCCATGGTAA<br>R (SEQ ID NO: 14): TATGCTACGCCGGCACTAA |

TABLE 9-continued

Summary statistics for Simple Sequence Repeat primers used to assess genetic relatedness among 'XSA 11377' and St. Augustinegrass commercial cultivars.

| Primer Pair No. | Primer Name | No. of alleles amplified | Primer Sequence |
|---|---|---|---|
| 8 | 28514 | 7 | F (SEQ ID NO: 15): CACGGAAATGTGGTTCATGTTT R (SEQ ID NO: 16): CTTGAATCGCACGGTCCATA |
| 9 | 29269 | 8 | F (SEQ ID NO: 17): ACCACCAACGGCAACAAC R (SEQ ID NO: 18): TCATCACATGATTGCATGCTT |
| 10 | 29525 | 10 | F (SEQ ID NO: 19): AGGCGCCTGCAGACATAGTA R (SEQ ID NO: 20): GGTATGGCTGCTCGTGTCA |
| 11 | 29919 | 11 | F (SEQ ID NO: 21): AAGCTGCTGGGGTGAGGT R (SEQ ID NO: 22): TTGAACAAGTTATTGGTGAAATGC |
| 12 | 4327 | 9 | F (SEQ ID NO: 23): AGGATTTGGTTTTCCTCTTCG R (SEQ ID NO: 24): ACAGCCTCGGAGCGAACT |
| 13 | 4930 | 7 | F (SEQ ID NO: 25): AAGTGATCGATCCCATCCTA R (SEQ ID NO: 26): CCTCAAAGCACGCACGTA |
| 14 | 6099 | 7 | F (SEQ ID NO: 27): AACGGGACATCCGGAGAG R (SEQ ID NO: 28): TCGAAGACGACGCACTTG |
| 15 | 5258 | 6 | F (SEQ ID NO: 29): CTGCCATCTGGAGCACAAC R (SEQ ID NO: 30): TGCTCTACTTCTTGATCCCAAAA |
| 16 | 6818 | 5 | F (SEQ ID NO: 31): TGTACTACCATGGAGATCAACTTGT R (SEQ ID NO: 32): TGGTATGGTGTGACTACCTTGTG |
| Total | | 134 | |
| Average | | 8.38 | |
| Min | | 5 | |
| Max | | 13 | |

REFERENCES

Busey P, Reinert J A, Atilano R A (1982) Genetic and environmental determinants of zoysiagrass adaptation in a subtropical region. J Amer Soc Hort Sci 107:79-82

Busey P, Davis E H (1991) Turfgrass in the shade environment. Florida State Hort Soc Proc 104: 353-358

Busey P (2003) St. Augustinegrass, *Stenotaphrum secundatum* (Walt.) Kuntze pp 309-329 In: M D Casler and R R Duncan, Turfgrass Biology, Genetics, and Breeding, John Wiley & Sons, Hoboken, NJ Dice, L. R. 1945. Measures of the amount of ecologic association between species. Ecology 26: 297-302.

Carbajal, E. M., B. Ma, M. C. Zuelta, W. C. Reynolds, C. Arellano, L. P. Tredway, and S. R. Milla-Lewis. 2021. Identification of sources of resistance to gray leaf spot in *Stenotaphrum* germplasm. Crop Science 61: 3069-3079 https://doi.org/10.1002/csc2.20371

Jha, P. 2018. Assessing sod production characteristics: sod handling quality and sod tensile strength of warm-season turfgrasses. MS Thesis from Oklahoma State University. December 2018. Available online.

Milla-Lewis, S. R., Zuleta, M. C., Van Esbroeck, G. A., Quesenberry, K. H., Kenworthy, K. E. 2013. Cytological and molecular characterization of genetic diversity in *Stenotaphrum*. Crop Sci. 53(1):296-308.

Miller, G. L. 2021. 2021 Sod producers' report for North Carolina. NC State Extension Publication AG-809, May 13, 2021. Available online.

Morris, K. N., and R. C. Shearman. 1998. NTEP turfgrass evaluation guidelines.

Mulkey, S. E., Zuleta, M. C., Van Esbroeck, G. A., Lu, H. J., Kenworthy, K. E., Milla-Lewis, S. R. 2013. Genetic analysis of a St. Augustinegrass germplasm collection using AFLP markers and flow cytometry. Intl. Turfgrass Soc. Res. J. 12:281-291

Mulkey, S. E., Zuleta, M. C., Keebler, J. E., Schaff, J. E., and Milla-Lewis, S. R. 2014. Development and characterization of simple sequence repeat (SSR) markers for St. Augustinegrass (*Stenotaphrum secundatum* (Walt.) Kuntze). Crop Sci. 54:401-412

Rohlf, F. J. 2000. NTSYS-PC: Numerical taxonomy and multivariate analysis system, version 2.2. Exeter Software, Setauket, NY.

Sokal, R. R., and Michener, C. D. 1958. A statistical method for evaluating systematic relationships. Univ. Kansas Sci. Bull. 28: 1409-1438.

SEQUENCE LISTING

```
Sequence total quantity: 32
SEQ ID NO: 1            moltype = DNA  length = 24
FEATURE                 Location/Qualifiers
source                  1..24
                        mol_type = other DNA
                        organism = synthetic construct
SEQUENCE: 1
ttcatctgtt gccaatatac atca                                          24

SEQ ID NO: 2            moltype = DNA  length = 21
FEATURE                 Location/Qualifiers
source                  1..21
                        mol_type = other DNA
                        organism = synthetic construct
SEQUENCE: 2
gggtaggaat gaggaatcca a                                             21

SEQ ID NO: 3            moltype = DNA  length = 18
```

-continued

```
FEATURE                 Location/Qualifiers
source                  1..18
                        mol_type = other DNA
                        organism = synthetic construct
SEQUENCE: 3
ctcgcgccaa agaagagg                                                 18

SEQ ID NO: 4            moltype = DNA  length = 17
FEATURE                 Location/Qualifiers
source                  1..17
                        mol_type = other DNA
                        organism = synthetic construct
SEQUENCE: 4
cccgggcttg aattgac                                                  17

SEQ ID NO: 5            moltype = DNA  length = 20
FEATURE                 Location/Qualifiers
source                  1..20
                        mol_type = other DNA
                        organism = synthetic construct
SEQUENCE: 5
acctggtact gcaaccgtct                                               20

SEQ ID NO: 6            moltype = DNA  length = 25
FEATURE                 Location/Qualifiers
source                  1..25
                        mol_type = other DNA
                        organism = synthetic construct
SEQUENCE: 6
tctctctagt ctctctgaac tgagc                                         25

SEQ ID NO: 7            moltype = DNA  length = 24
FEATURE                 Location/Qualifiers
source                  1..24
                        mol_type = other DNA
                        organism = synthetic construct
SEQUENCE: 7
tcctacaaga caatcaaatc tgga                                          24

SEQ ID NO: 8            moltype = DNA  length = 22
FEATURE                 Location/Qualifiers
source                  1..22
                        mol_type = other DNA
                        organism = synthetic construct
SEQUENCE: 8
gggcacacaa ttgagttcag ta                                            22

SEQ ID NO: 9            moltype = DNA  length = 18
FEATURE                 Location/Qualifiers
source                  1..18
                        mol_type = other DNA
                        organism = synthetic construct
SEQUENCE: 9
ggcctccgac gaggaata                                                 18

SEQ ID NO: 10           moltype = DNA  length = 20
FEATURE                 Location/Qualifiers
source                  1..20
                        mol_type = other DNA
                        organism = synthetic construct
SEQUENCE: 10
actagatcca cggagcagga                                               20

SEQ ID NO: 11           moltype = DNA  length = 22
FEATURE                 Location/Qualifiers
source                  1..22
                        mol_type = other DNA
                        organism = synthetic construct
SEQUENCE: 11
cacgaggctg tactaccact ca                                            22

SEQ ID NO: 12           moltype = DNA  length = 23
FEATURE                 Location/Qualifiers
source                  1..23
                        mol_type = other DNA
                        organism = synthetic construct
SEQUENCE: 12
tgaaatgtta agtttgtgcg tgt                                           23
```

-continued

```
SEQ ID NO: 13          moltype = DNA  length = 20
FEATURE                Location/Qualifiers
source                 1..20
                       mol_type = other DNA
                       organism = synthetic construct
SEQUENCE: 13
gagtgctagg cccatggtaa                                              20

SEQ ID NO: 14          moltype = DNA  length = 19
FEATURE                Location/Qualifiers
source                 1..19
                       mol_type = other DNA
                       organism = synthetic construct
SEQUENCE: 14
tatgctacgc cggcactaa                                               19

SEQ ID NO: 15          moltype = DNA  length = 22
FEATURE                Location/Qualifiers
source                 1..22
                       mol_type = other DNA
                       organism = synthetic construct
SEQUENCE: 15
cacggaaatg tggttcatgt tt                                           22

SEQ ID NO: 16          moltype = DNA  length = 20
FEATURE                Location/Qualifiers
source                 1..20
                       mol_type = other DNA
                       organism = synthetic construct
SEQUENCE: 16
cttgaatcgc acggtccata                                              20

SEQ ID NO: 17          moltype = DNA  length = 18
FEATURE                Location/Qualifiers
source                 1..18
                       mol_type = other DNA
                       organism = synthetic construct
SEQUENCE: 17
accaccaacg gcaacaac                                                18

SEQ ID NO: 18          moltype = DNA  length = 21
FEATURE                Location/Qualifiers
source                 1..21
                       mol_type = other DNA
                       organism = synthetic construct
SEQUENCE: 18
tcatcacatg attgcatgct t                                            21

SEQ ID NO: 19          moltype = DNA  length = 20
FEATURE                Location/Qualifiers
source                 1..20
                       mol_type = other DNA
                       organism = synthetic construct
SEQUENCE: 19
aggcgcctgc agacatagta                                              20

SEQ ID NO: 20          moltype = DNA  length = 19
FEATURE                Location/Qualifiers
source                 1..19
                       mol_type = other DNA
                       organism = synthetic construct
SEQUENCE: 20
ggtatggctg ctcgtgtca                                               19

SEQ ID NO: 21          moltype = DNA  length = 18
FEATURE                Location/Qualifiers
source                 1..18
                       mol_type = other DNA
                       organism = synthetic construct
SEQUENCE: 21
aagctgctgg ggtgaggt                                                18

SEQ ID NO: 22          moltype = DNA  length = 24
FEATURE                Location/Qualifiers
source                 1..24
                       mol_type = other DNA
                       organism = synthetic construct
```

-continued

```
SEQUENCE: 22
ttgaacaagt tattggtgaa atgc                                          24

SEQ ID NO: 23          moltype = DNA  length = 21
FEATURE                Location/Qualifiers
source                 1..21
                       mol_type = other DNA
                       organism = synthetic construct
SEQUENCE: 23
aggatttggt tttcctcttc g                                             21

SEQ ID NO: 24          moltype = DNA  length = 18
FEATURE                Location/Qualifiers
source                 1..18
                       mol_type = other DNA
                       organism = synthetic construct
SEQUENCE: 24
acagcctcgg agcgaact                                                 18

SEQ ID NO: 25          moltype = DNA  length = 20
FEATURE                Location/Qualifiers
source                 1..20
                       mol_type = other DNA
                       organism = synthetic construct
SEQUENCE: 25
aagtgatcga tcccatccta                                               20

SEQ ID NO: 26          moltype = DNA  length = 18
FEATURE                Location/Qualifiers
source                 1..18
                       mol_type = other DNA
                       organism = synthetic construct
SEQUENCE: 26
cctcaaagca cgcacgta                                                 18

SEQ ID NO: 27          moltype = DNA  length = 18
FEATURE                Location/Qualifiers
source                 1..18
                       mol_type = other DNA
                       organism = synthetic construct
SEQUENCE: 27
aacgggacat ccggagag                                                 18

SEQ ID NO: 28          moltype = DNA  length = 18
FEATURE                Location/Qualifiers
source                 1..18
                       mol_type = other DNA
                       organism = synthetic construct
SEQUENCE: 28
tcgaagacga cgcacttg                                                 18

SEQ ID NO: 29          moltype = DNA  length = 19
FEATURE                Location/Qualifiers
source                 1..19
                       mol_type = other DNA
                       organism = synthetic construct
SEQUENCE: 29
ctgccatctg gagcacaac                                                19

SEQ ID NO: 30          moltype = DNA  length = 23
FEATURE                Location/Qualifiers
source                 1..23
                       mol_type = other DNA
                       organism = synthetic construct
SEQUENCE: 30
tgctctactt cttgatccca aaa                                           23

SEQ ID NO: 31          moltype = DNA  length = 25
FEATURE                Location/Qualifiers
source                 1..25
                       mol_type = other DNA
                       organism = synthetic construct
SEQUENCE: 31
tgtactacca tggagatcaa cttgt                                         25

SEQ ID NO: 32          moltype = DNA  length = 23
FEATURE                Location/Qualifiers
source                 1..23
```

-continued

```
                    mol_type = other DNA
                    organism = synthetic construct
SEQUENCE: 32
tggtatggtg tgactacctt gtg                                    23
```

I claim:

1. A new and distinct cultivar of *Stenotaphrum secundatum* St. Augustinegrass plant named 'XSA 11377', substantially as illustrated and described herein.

* * * * *